United States Patent
Li et al.

(10) Patent No.: US 10,667,709 B2
(45) Date of Patent: Jun. 2, 2020

(54) HYBRID DIAMOND-POLYMER THIN FILM SENSORS AND FABRICATION METHOD

(71) Applicants: Board of Trustees of Michigan State University, East Lansing, MI (US); Fraunhofer USA, East Lansing, MI (US)

(72) Inventors: Wen Li, Okemos, MI (US); Bin Fan, East Lansing, MI (US); Robert Rechenberg, Vermontville, MI (US); Michael Becker, East Lansing, MI (US); Cory Rusinek, Okemos, MI (US)

(73) Assignees: Board of Trustees of Michigan State University, East Lansing, MI (US); Fraunhofer USA, East Lansing, MI (US)

( * ) Notice: Subject to any disclaimer, the term of this patent is extended or adjusted under 35 U.S.C. 154(b) by 0 days.

(21) Appl. No.: 16/301,915

(22) PCT Filed: May 26, 2017

(86) PCT No.: PCT/US2017/034745
§ 371 (c)(1),
(2) Date: Nov. 15, 2018

(87) PCT Pub. No.: WO2017/205781
PCT Pub. Date: Nov. 30, 2017

(65) Prior Publication Data
US 2019/0282110 A1    Sep. 19, 2019

Related U.S. Application Data

(60) Provisional application No. 62/342,266, filed on May 27, 2016.

(51) Int. Cl.
*H01L 21/78* (2006.01)
*B23K 26/53* (2014.01)
(Continued)

(52) U.S. Cl.
CPC .......... *A61B 5/04001* (2013.01); *B81B 3/007* (2013.01); *B81B 7/0025* (2013.01);
(Continued)

(58) Field of Classification Search
CPC .......... H01L 21/02595; H01L 21/3065; H01L 21/76805; H01L 21/02491;
(Continued)

(56) References Cited

U.S. PATENT DOCUMENTS

| 4,394,712 A | * | 7/1983 | Anthony | ............. H01L 23/5385 |
| | | | | 174/256 |
| 5,468,681 A | * | 11/1995 | Pasch | .................. G03F 7/70433 |
| | | | | 438/108 |

(Continued)

FOREIGN PATENT DOCUMENTS

WO    WO-2015056175 A1    4/2015

OTHER PUBLICATIONS

International Search Report and Written Opinion of the International Searching Authority regarding International Application No. PCT/US2017/034745, dated Oct. 3, 2017.
(Continued)

*Primary Examiner* — Caridad Everhart
(74) *Attorney, Agent, or Firm* — Harness, Dickey & Pierce, PLC

(57) ABSTRACT

An implantable device is provided. The implantable device includes a flexible polymeric substrate that extends through an aperture in an electrically conductive material to form an anchor that partially covers the electrically conductive material. Methods for fabricating the implantable device are also provided.

24 Claims, 24 Drawing Sheets

(51) Int. Cl.
- *A61B 5/04* (2006.01)
- *H01L 21/02* (2006.01)
- *H01L 21/033* (2006.01)
- *H01L 21/04* (2006.01)
- *H01L 21/3065* (2006.01)
- *H01L 21/3213* (2006.01)
- *B81B 3/00* (2006.01)
- *B81B 7/00* (2006.01)

(52) U.S. Cl.
CPC .. *H01L 21/02164* (2013.01); *H01L 21/02381* (2013.01); *H01L 21/02527* (2013.01); *H01L 21/0331* (2013.01); *H01L 21/0405* (2013.01); *H01L 21/3065* (2013.01); *H01L 21/32137* (2013.01); *A61B 2562/0209* (2013.01); *B81B 2201/0214* (2013.01); *B81B 2203/04* (2013.01)

(58) Field of Classification Search
CPC ......... H01L 21/02164; H01L 21/02381; H01L 21/02527; H01L 21/0331; H01L 21/0405; H01L 21/32137; A61B 2562/0209
See application file for complete search history.

(56) References Cited

U.S. PATENT DOCUMENTS

| | | | |
|---|---|---|---|
| 5,470,790 A * | 11/1995 | Myers | H01L 21/32133 438/625 |
| 5,877,559 A * | 3/1999 | Takayama | H01L 23/49811 257/737 |
| 6,335,224 B1 | 1/2002 | Peterson et al. | |
| 7,029,829 B2 | 4/2006 | Stark et al. | |
| 8,278,725 B2 | 10/2012 | Tripathy et al. | |
| 8,536,667 B2 | 9/2013 | de Graff et al. | |
| 9,241,651 B2 | 1/2016 | Fedder et al. | |
| 2009/0152109 A1* | 6/2009 | Whitehead | G01N 27/307 204/400 |
| 2011/0212555 A1 | 9/2011 | Tredwell et al. | |
| 2012/0165759 A1 | 6/2012 | Rogers et al. | |
| 2013/0213823 A1 | 8/2013 | Arumugam et al. | |
| 2014/0193979 A1 | 7/2014 | Or et al. | |
| 2015/0343202 A1 | 12/2015 | Picaud et al. | |
| 2016/0086807 A1 | 3/2016 | Park et al. | |

OTHER PUBLICATIONS

Bergonzo et al., "3D shaped mechanically flexible diamond microelectrode arrays for eye implant applications: The MEDINAS project." IRBM, vol. 32, No. 2, pp. 91-94 (2011).

Bernard et al., "Non-destructive determination of the boron concentration of heavily doped metallic diamond thin films from Raman spectroscopy." Diamond and Related Materials, vol. 13, No. 2, pp. 282-286 (2004).

Fan et al., "Fabrication of polycrystalline diamond on a flexible Parylene substrate." 2015 Transducers—2015 18th International Conference on Solid-State Sensors, Actuators and Microsystems (Transducers), IEEE, pp. 892-895 (2015).

Hess et al., "Diamond-on-Polymer Microelectrode Arrays Fabricated Using a Chemical Release Transfer Process." Journal of Microelectromechanical Systems, vol. 20, No. 4, pp. 867-875 (2011).

Hupert et al., "Conductive diamond thin-films in electrochemistry." Diamond and Related Materials, vol. 12, No. 10-11, pp. 1940-1949 (2003).

Kraft, "Doped Diamond: A Compact Review on a New, Versatile Electrode Material." International Journal of Electrochemical Science, vol. 2, pp. 355-385 (2007).

Musaev et al., "UV laser ablation of parylene films from gold substrates." Journal of Materials Science, vol. 46, No. 1, pp. 183-187 (2011).

* cited by examiner

HYBRID DIAMOND-POLYMER THIN FILM SENSORS AND FABRICATION METHOD

CROSS-REFERENCE TO RELATED APPLICATIONS

This application is a National Phase Entry of International Application Serial No. PCT/US2017/034745, filed on May 26, 2017, which claims the benefit of U.S. Provisional Application No. 62/342,266, filed on May 27, 2016, both of which are incorporated herein by reference.

GOVERNMENT RIGHTS

This invention was made with government support under CBET1264772 and ECCS1407880 awarded by the National Science Foundation, and under NS096637 awarded by the National Institutes of Health. The government has certain rights in the invention.

FIELD

The present disclosure relates to flexible implantable sensors and methods of making the flexible implantable sensors.

BACKGROUND

This section provides background information related to the present disclosure which is not necessarily prior art.

Sensors are often used to detect electrical and chemical signals in biological tissue. For example, neural probes are used to detect electrical and chemical signals in brains, and to stimulate specific neurons or regions in brains. Recently, MicroElectroMechanical Systems (MEMS) are used to manufacture devices on a very small scale by micromachining. Although MEMS can be used to fabricate probes or sensors to be implanted in various biological tissues, the field of NeuroMEMS is now providing very small neural probes that may be implanted into brains. Micromachining neural probes using NeuroMEMS often includes depositing hard and rigid conductive materials rigid substrates.

Sensors and probes fabricated with electrically conductive materials that are hard and rigid due to a high Young's modulus are often not ideal for implanting into biological materials. For example, a stiffness mismatch between the hard and rigid electrically conductive material and brain tissue may cause negative tissue responses, irritation, and/or irreversible tissue damage. Stiffness mismatches are also problematic in regard to wearable sensors because a rigid material cannot have a conformal contact to skin, which causes deterioration or sensing performance over time.

Small and flexible probes and sensors are often advantageous over larger and rigid neural probes because, when implanted in brains for example, they result in less neural damage upon implantation and specific neurons may be targeted more closely. However, techniques used to fabricate small and flexible sensors and probes involve high temperatures and provide a low yield at a high cost. Therefore, there is a need to develop new flexible sensors at high yields and at a low cost.

SUMMARY

This section provides a general summary of the disclosure, and is not a comprehensive disclosure of its full scope or all of its features.

The current technology provides a method of fabricating a flexible device. The method includes generating a layer of $SiO_2$ on a surface of a substrate; disposing a layer of an electrically conductive material on the layer of $SiO_2$; removing a portion of the layer of an electrically conductive material to define a pattern in the remaining electrically conductive material, wherein the pattern includes a plurality of apertures that extend through the electrically conductive material and optionally through the layer of $SiO_2$ to the substrate; applying an etching compound into the apertures and etching the $SiO_2$ vertically downward to the Si substrate when the apertures do not extend through the layer of $SiO_2$ and etching a portion of the layer of $SiO_2$ horizontally beneath the electrically conductive material to form a plurality of undercuts; disposing a flexible polymeric material over the electrically conductive material, wherein the flexible polymeric material fills the undercuts and covers the electrically conductive material; and removing the substrate and the remainder of the $SiO_2$ by etching to generate the flexible device.

In one variation, the substrate includes silicon (Si), glass, or GaAs.

In one variation, the electrically conductive material includes boron doped polycrystalline diamond (BDD).

In one variation, the layer of an electrically conductive material has a thickness of from about 0.25 µm to about 10 µm.

In one variation, the removing a portion of the layer of an electrically conductive material is performed by photolithography.

In one variation, the photolithography includes disposing a metal layer onto the layer of an electrically conductive material, wherein the metal layer includes aluminum (Al), copper (Cu), or gold (Au); disposing a layer of photoresist on the metal layer; disposing a ultraviolet light (UV)-transparent mask on the layer of photoresist, wherein the UV-transparent mask includes a pattern that is not UV-transparent; and exposing the UV-transparent mask to UV light.

In one variation, the photolithography is performed by a lift-off method.

In one variation, the flexible polymeric material is parylene-C.

In one variation, the flexible polymeric material has a thickness of from about 1 µm to about 50 µm.

In one variation, the removing the substrate and the remainder of the $SiO_2$ by etching includes etching with potassium hydroxide (KOH), tetramethylammonium hydroxide (TMAH), or HF/nitric/acetic acid (HNA).

In one variation, the method further includes at least one of chemically modifying at least a portion of the electrically conductive material, disposing a ligand to at least a portion of the electrically conductive material, or disposing a thin film over at last a portion of the electrically conductive material.

In one variation, the method further includes attaching components to the electrically conductive material, wherein the components are selected from the group consisting of contact pads, contacts, light emitting diodes (LEDs), micro LEDs (pLEDs), wires, and combinations thereof.

In one variation, the flexible device is a brain implant.

The current technology also provides a method of fabricating a flexible device. The method includes generating a layer of $SiO_2$ on a surface of a silicon (Si) substrate; disposing a layer of boron doped polycrystalline diamond (BDD) on the layer of $SiO_2$; removing a portion of the BDD to define a pattern in the remaining BDD, wherein the pattern includes a plurality of apertures that extend through the BDD and optionally through the layer of $SiO_2$ to the substrate; applying an etching compound into the apertures and etching the $SiO_2$ vertically downward to the Si substrate when the apertures do not extend through the layer of $SiO_2$ and etching a portion of the layer of $SiO_2$ horizontally beneath the electrically conductive material to form a plurality of undercuts; disposing parylene-C over the BDD, wherein the parylene-C fills the undercuts and covers the BDD; removing a portion of the parylene_C located above the BDD; inverting the device and removing a top portion of the parylene-C and substantially all of the Si substrate; inverting the device and removing the remainder of the $SiO_2$; disposing additional parylene-C over top and bottom surfaces of the BDD by chemical vapor deposition; and removing the parylene-C disposed on the top surface of the BDD.

In one variation, the flexible device is a sensor including a working electrode, a counter electrode, and a reference electrode.

In one variation, the method further includes at least one of chemically modifying at least the working electrode, disposing a ligand to at least the working electrode, and disposing a thin film over at last the working electrode.

In one variation, the flexible device is configured to be implanted in neural tissue.

Additionally, the current technology provides a flexible device. The flexible device includes an electrically conductive material that defines a predetermined pattern, wherein the pattern includes at least one aperture that extends from a first surface of the electrically conductive material to a second opposing surface of the electrically conductive material; and a flexible polymeric substrate. The second surface of the electrically conductive material is disposed on the flexible polymer substrate and the flexible polymeric substrate extends through the at least one aperture from the second surface to the first surface and extends radially on the first surface about the at last one aperture to form an anchor that partially covers the electrically conductive material.

In one variation, the electrically conductive material is boron doped polycrystalline diamond (BDD), and the flexible polymeric substrate is parylene-C.

In one variation, the flexible device is an implantable probe or sensor having a Young's modulus that is closer to the Young's modulus of a human brain relative to the Young's modulus of boron doped polycrystalline diamond (BDD).

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 11A:
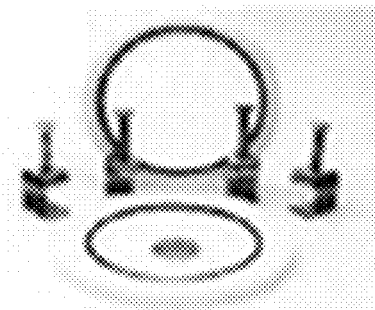
FIG. 11A is a photograph of a disassembled etching jig.
Figure 11B:
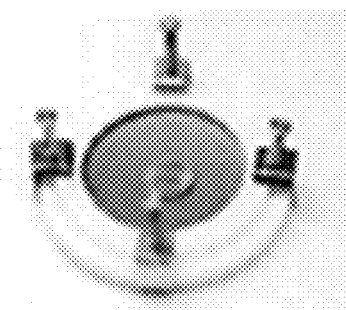
FIG. 11B is a photograph of an assembled etching jig.
Figure 11C:
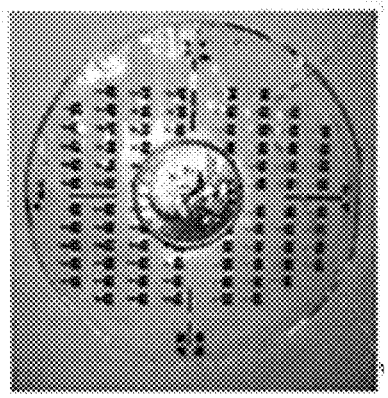
FIG. 11C is a photograph of boron-doped diamond patterns on a flexible parylene-C thin film after removing a Si substrate via KOH etching.
Figure 11D:
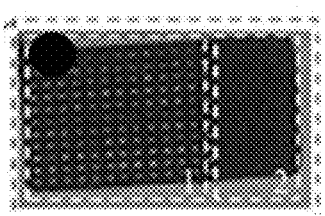
Figure 11E:
Figure 11F:
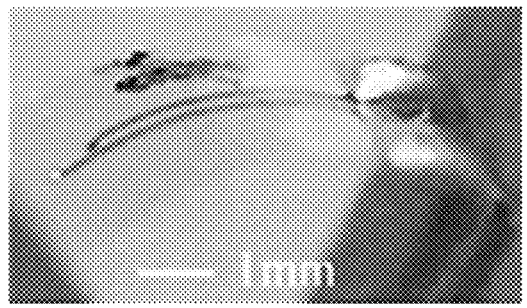
Figure 11G:
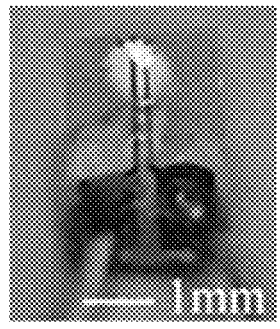
Figure 12A:
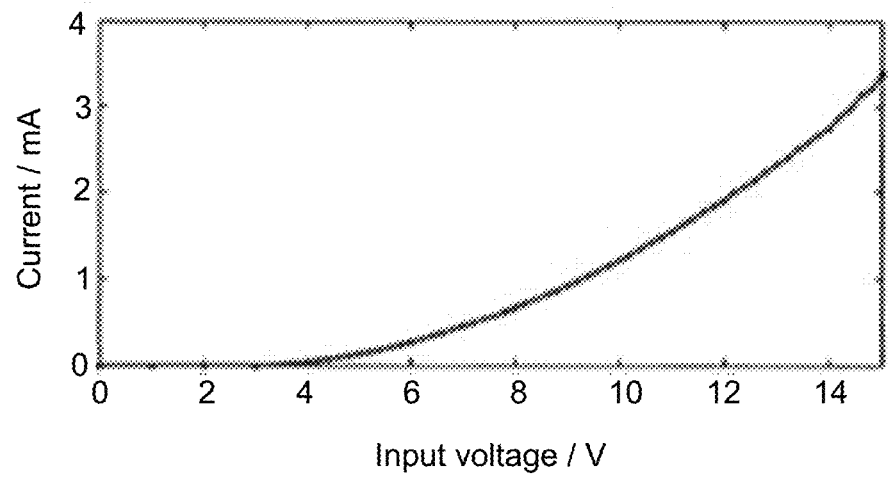
Figure 12B:
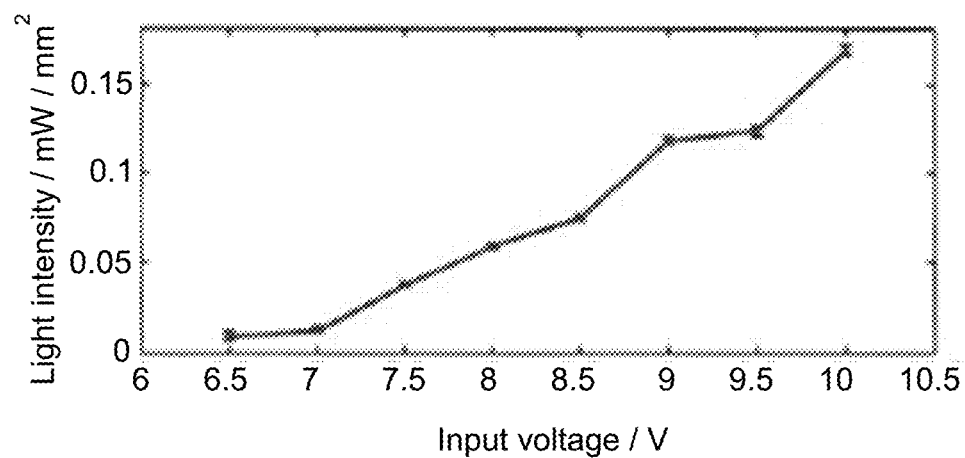
Figure 13A:
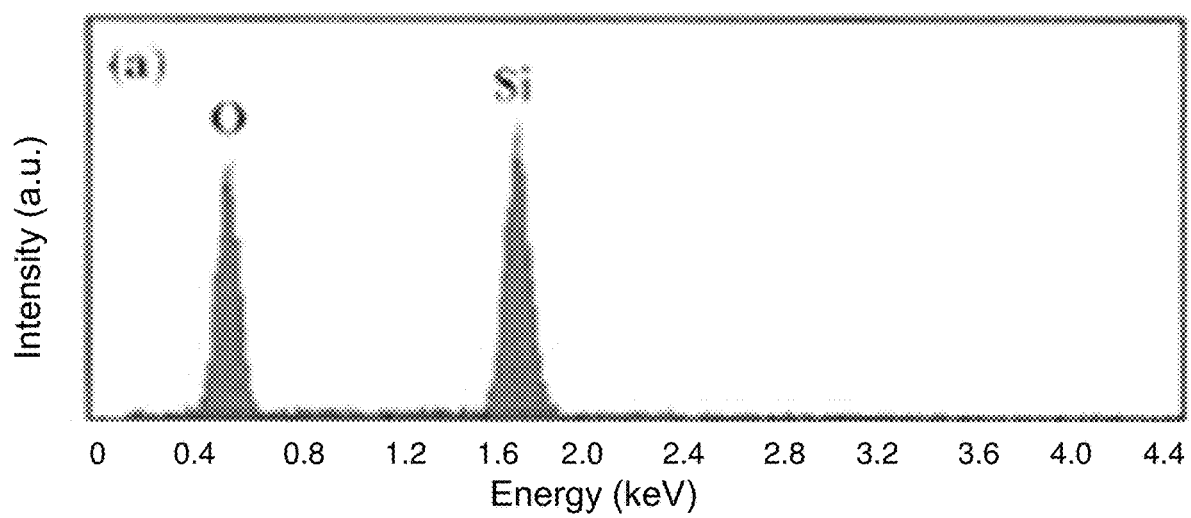
Figure 13B:
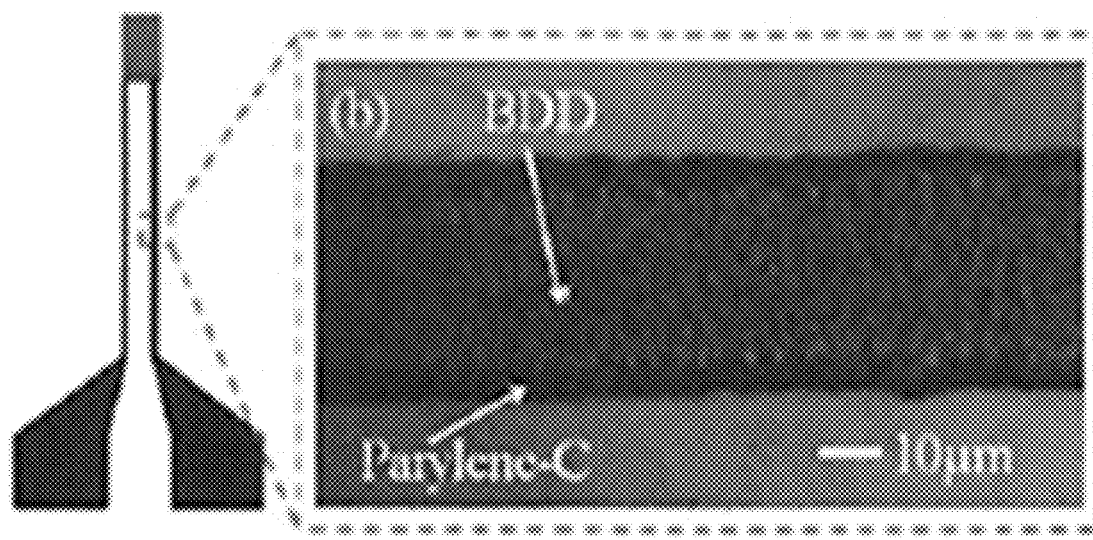
Figure 14A:
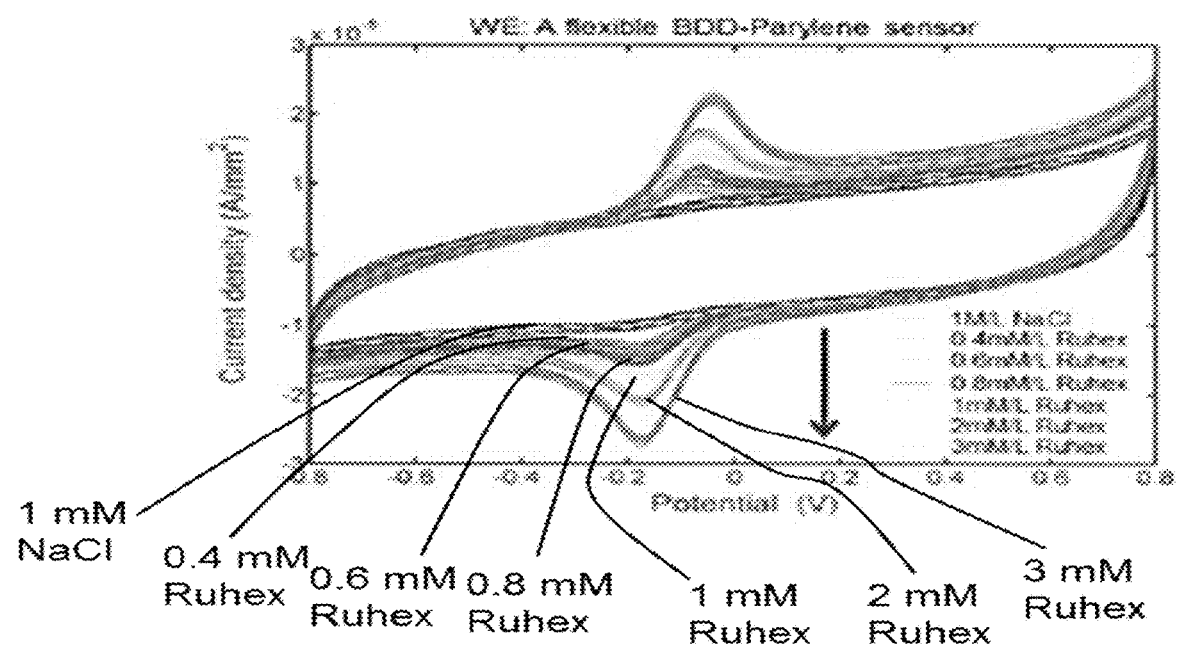
Figure 14B:
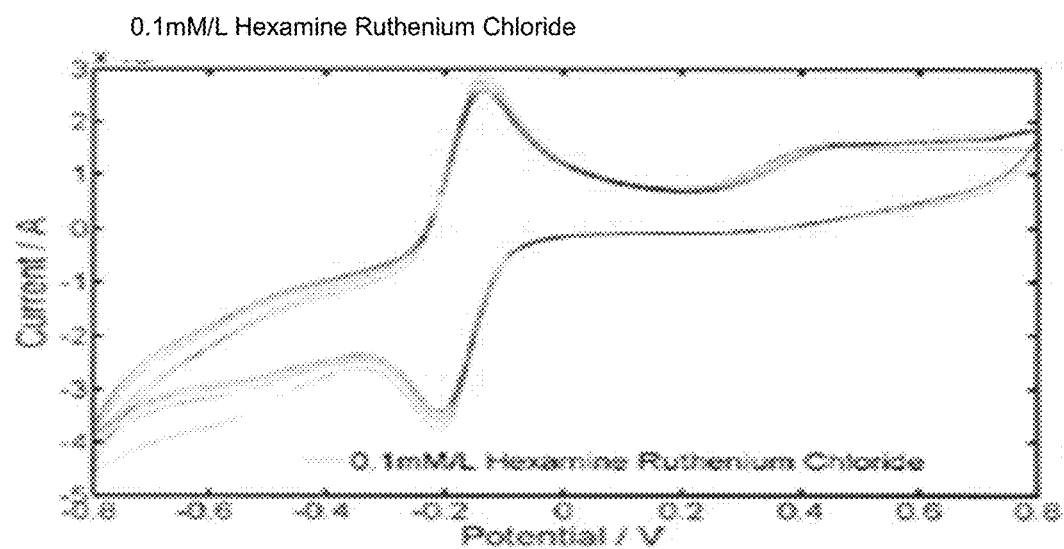
Figure 15:
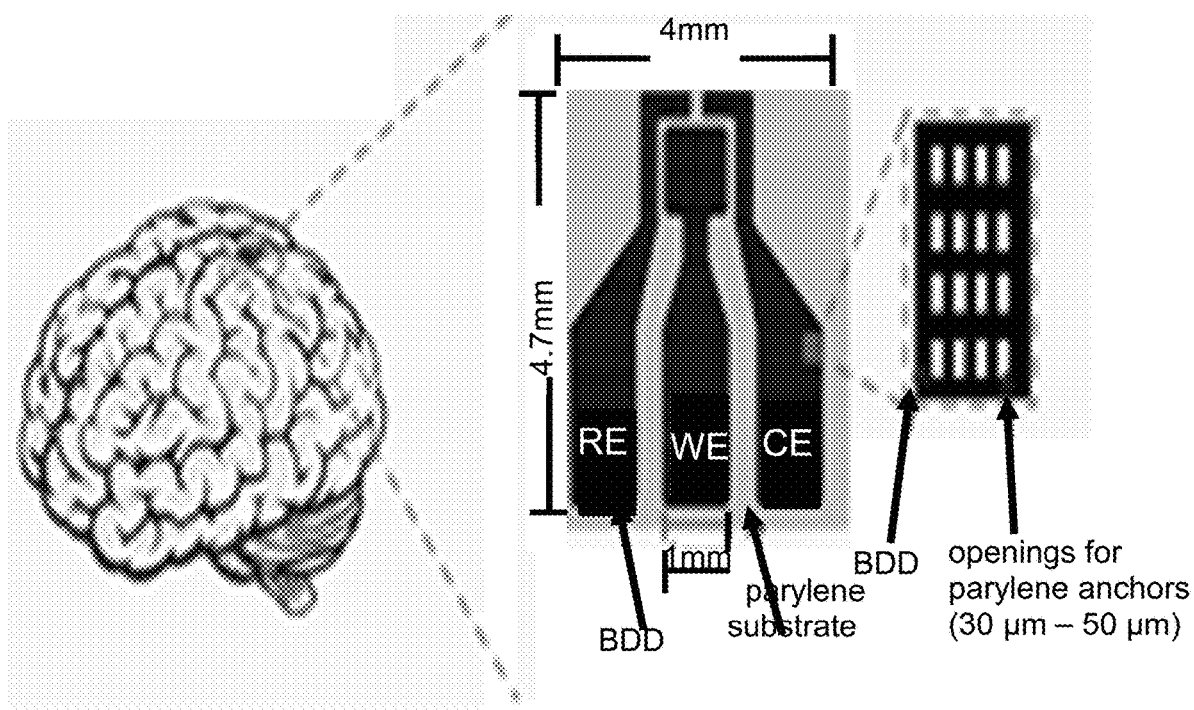
Figure 16:
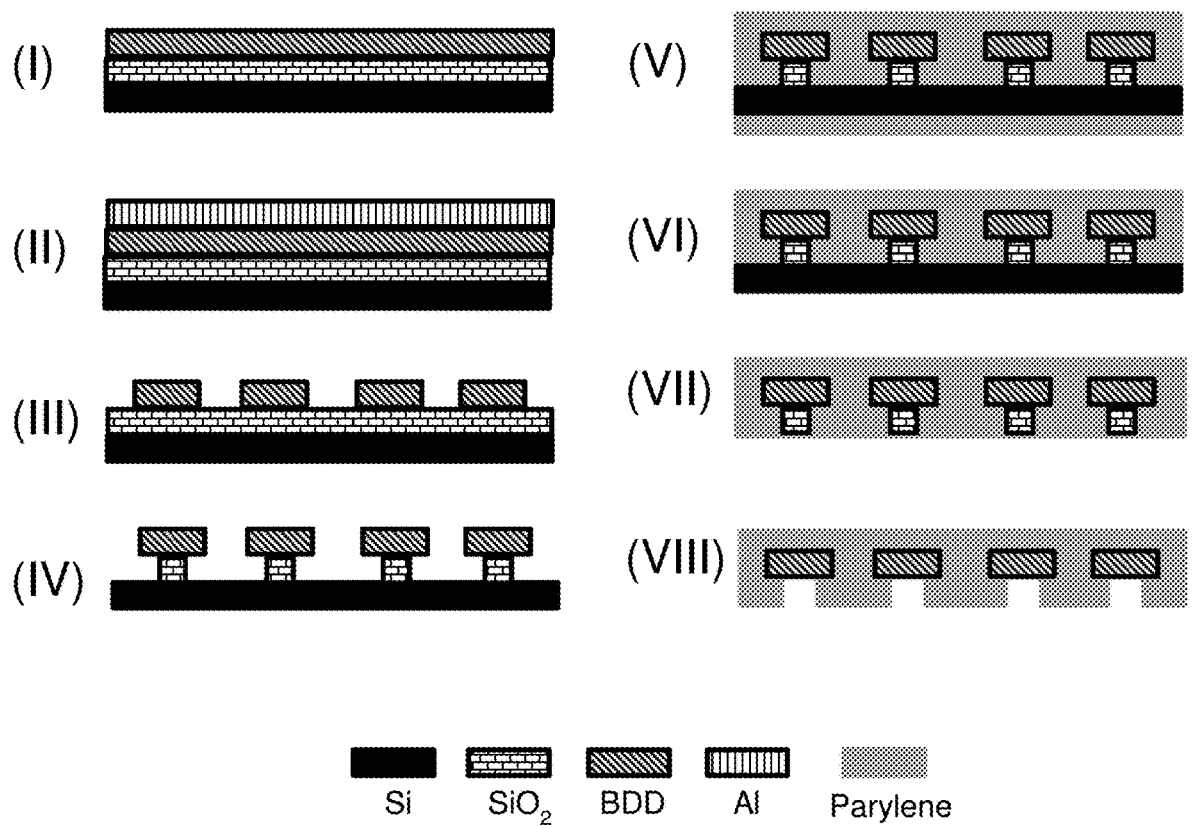
Figure 17A:
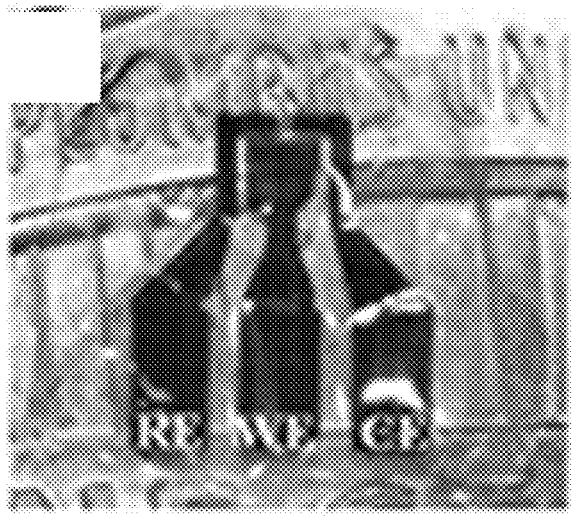
Figure 17B:
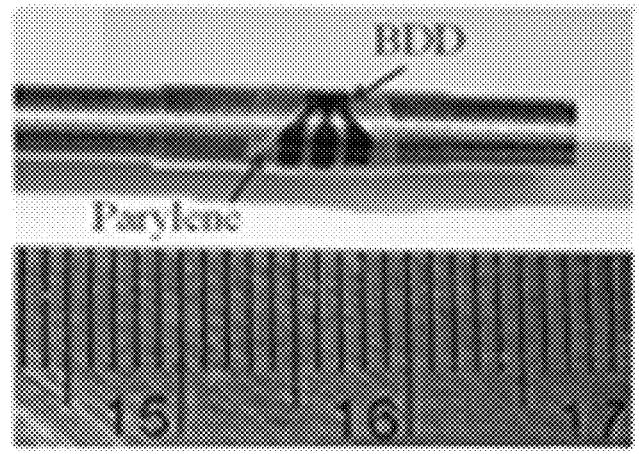
Figure 18A:
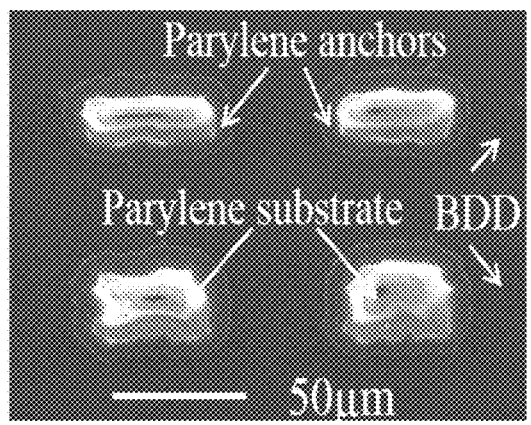
Figure 18B:
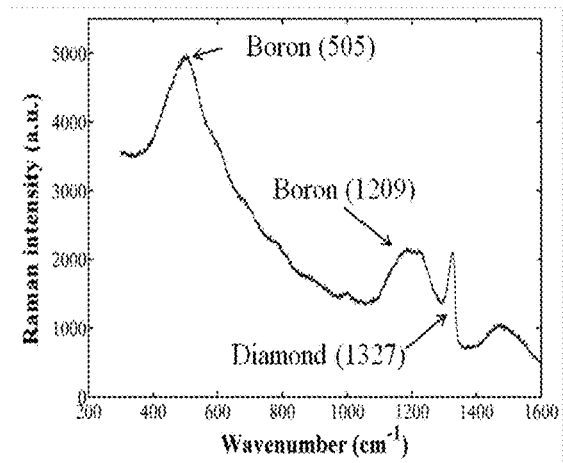
Figure 18C:
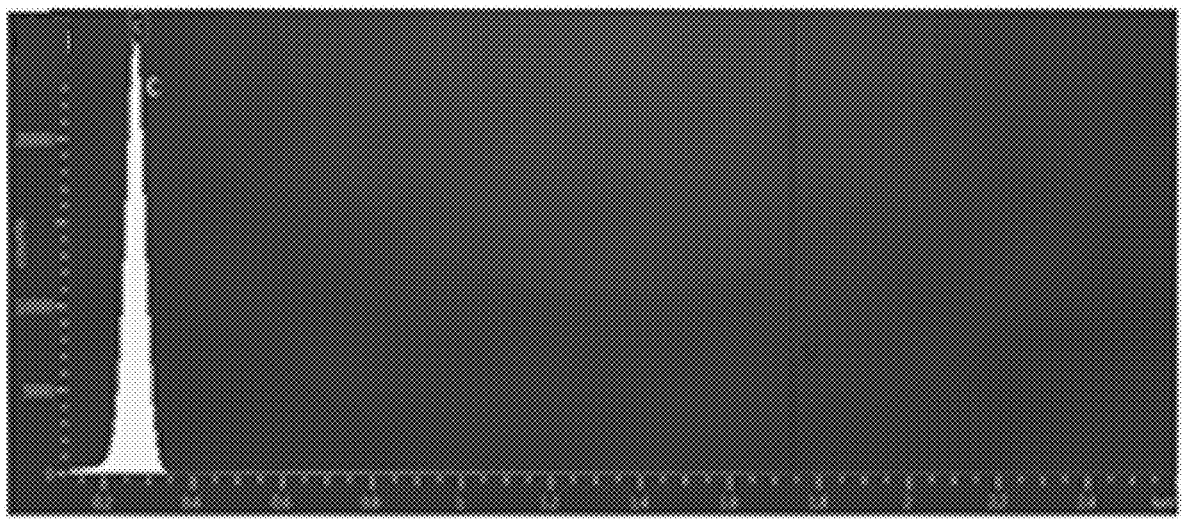
Figure 19A:
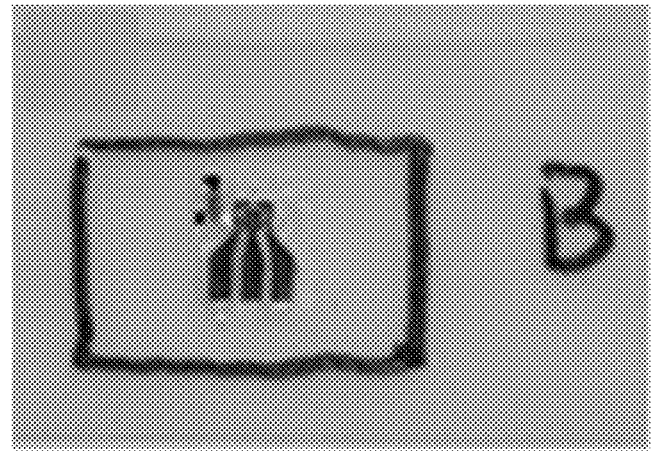
Figure 19B:
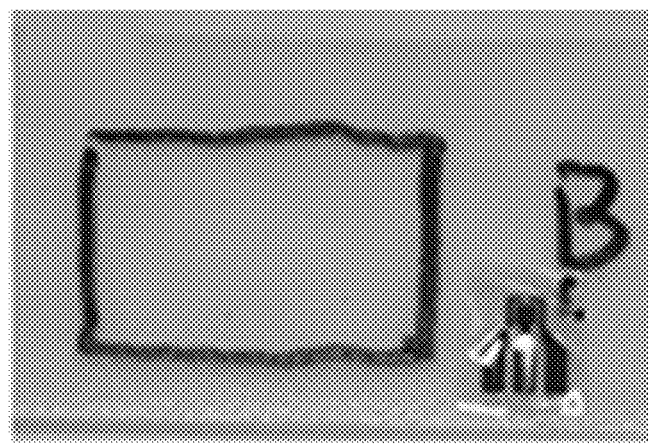
Figure 20A:
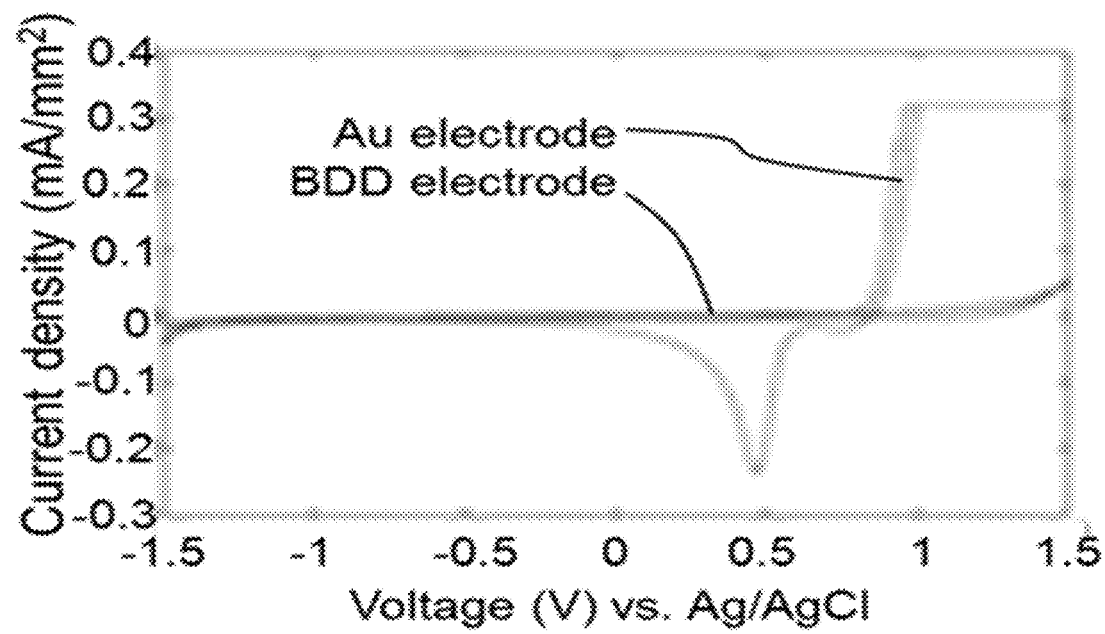
Figure 20B:
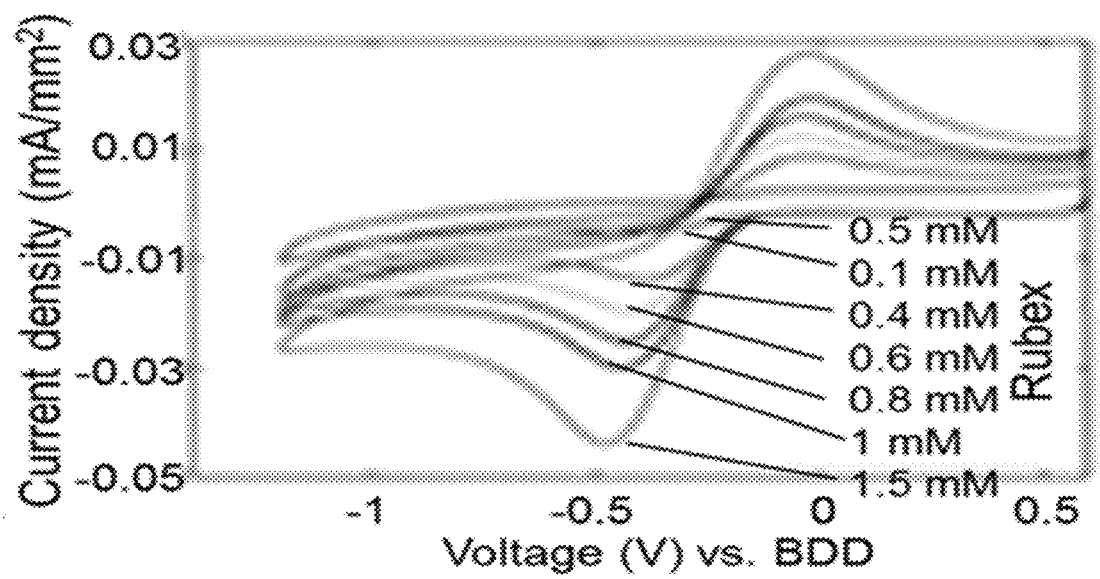
Figure 20C:
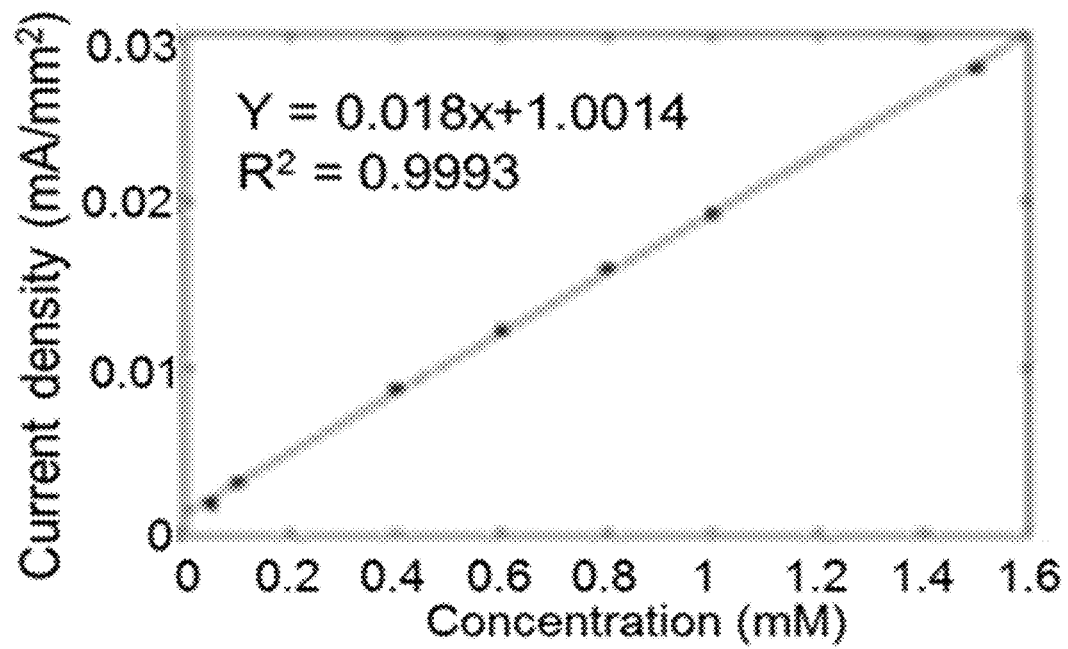
Figure 20D:
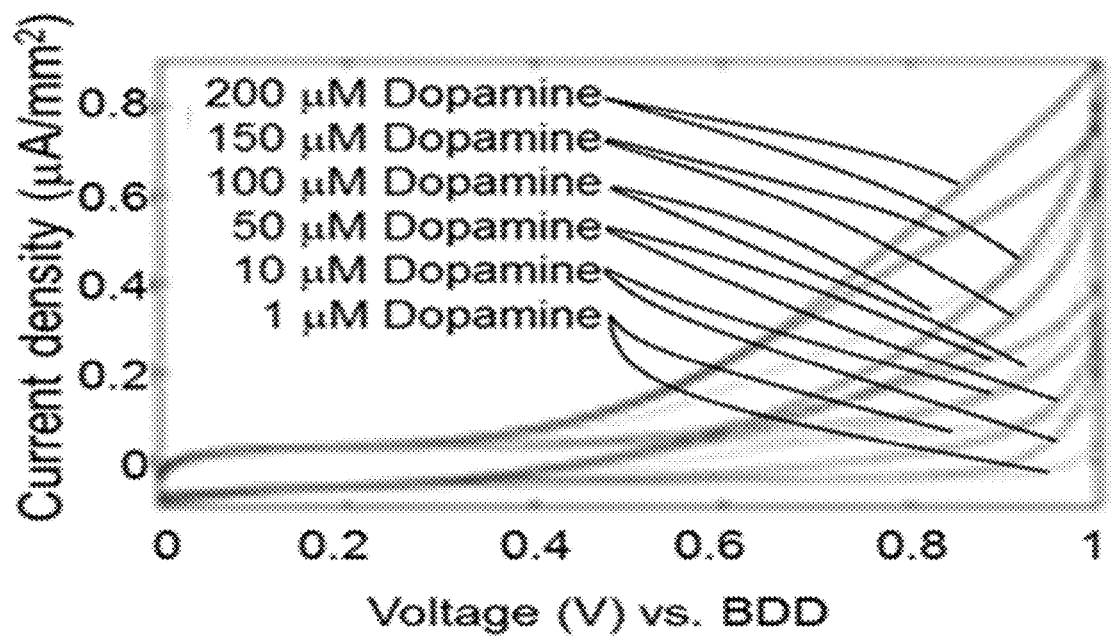
Figure 20E:
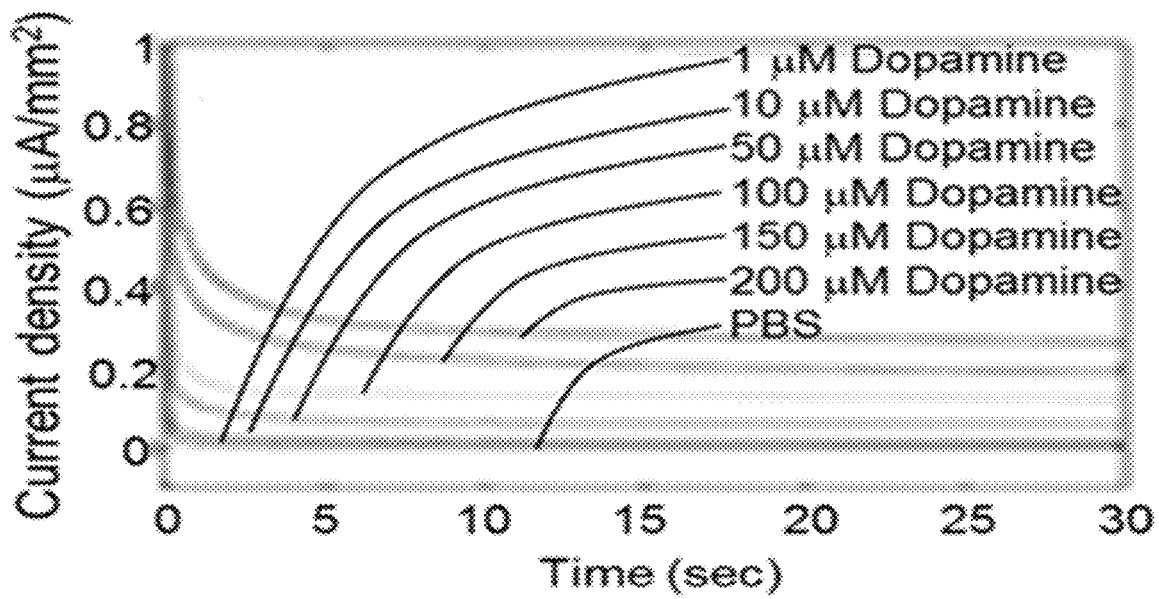
Figure 20F:
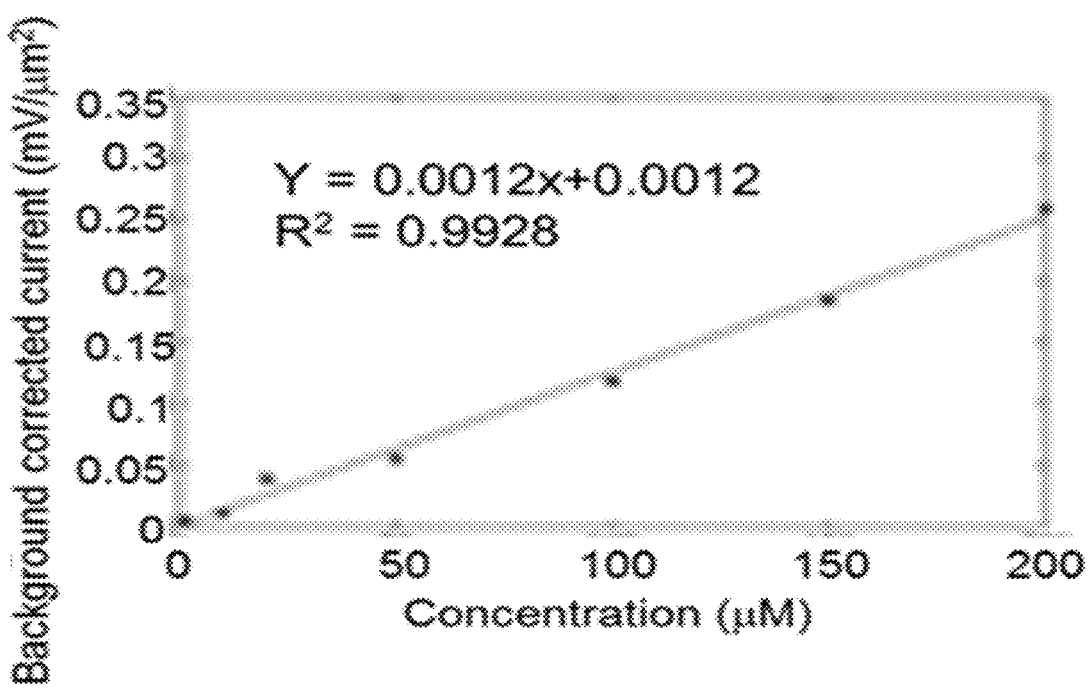
Figure 21:
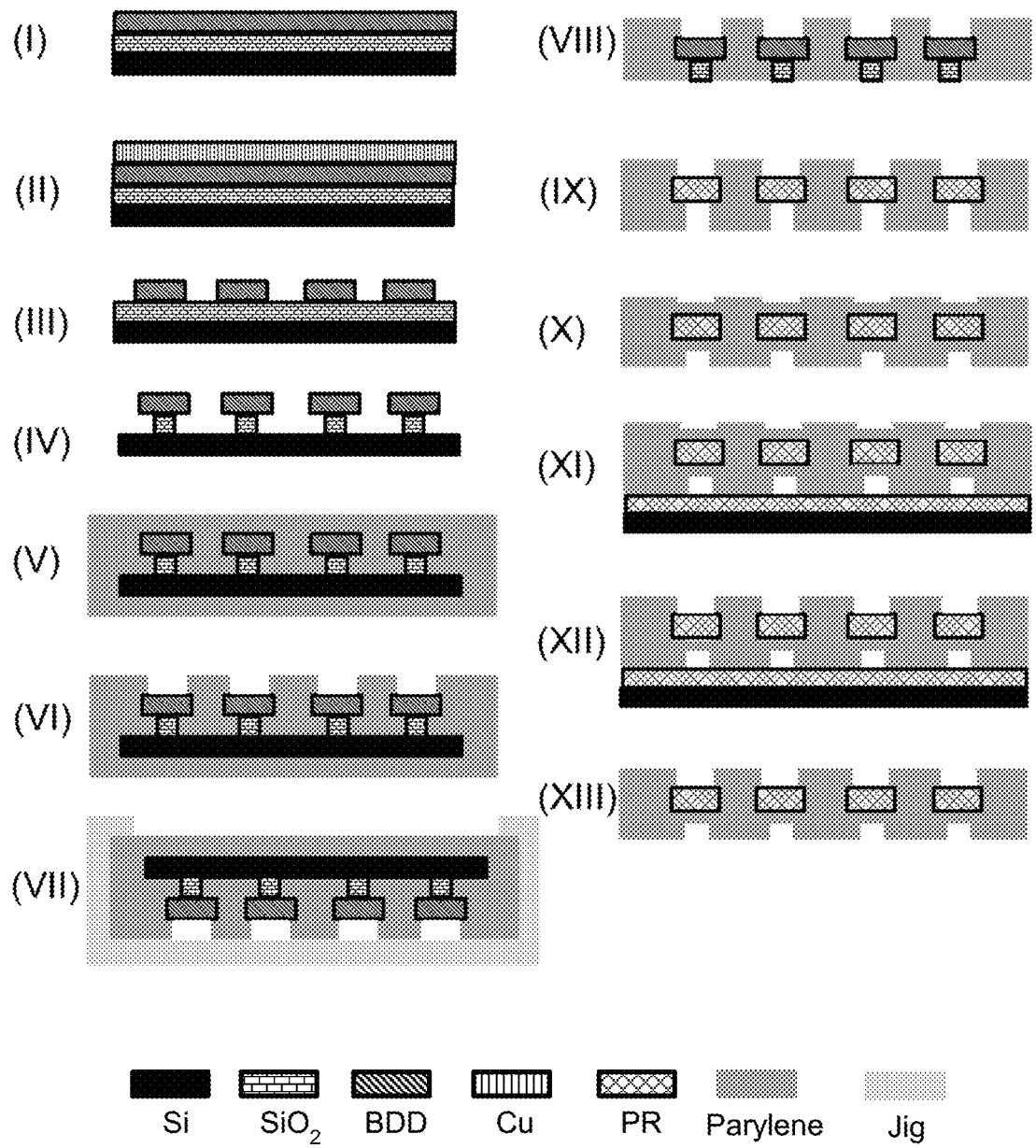
Figure 22A:
Figure 22B:
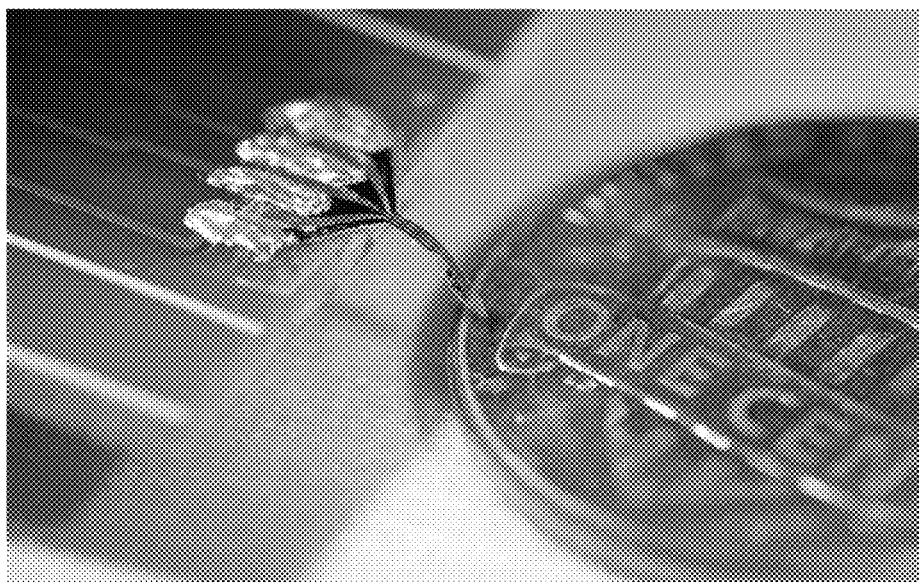
Figure 23A:
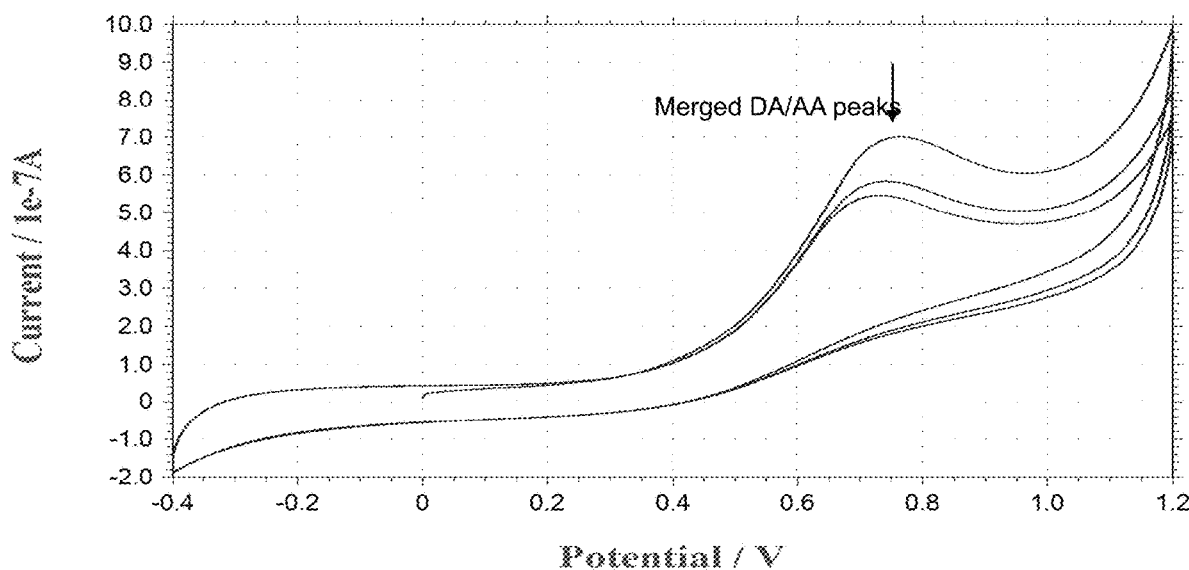
Figure 23B:
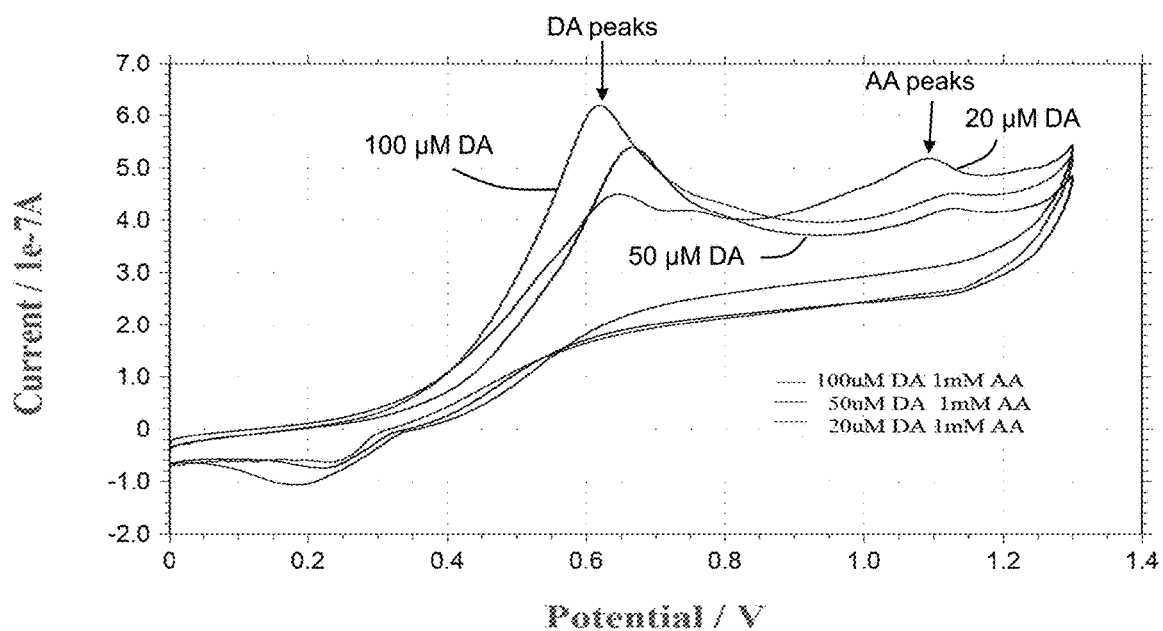

FIG. 11D is a photograph showing a close-up view of pads after KOH etching, wherein the dimension of the contact pads is 1.2 mm×0.9 mm without area 2 and 1.8 mm×0.9 mm with area 2;

FIG. 11E is a photograph showing a close-up view of pads after metal deposition and patterning;

FIG. 11F is a photograph showing the mechanical flexibility of fabricated LED probe;

FIG. 11G is a photograph showing powered up LED probe, which demonstrates the integrity of conductive boron-doped diamond leads and contacts FIG. 12A is an I-V curve of a fabricated boron-doped diamond probe;

FIG. 12B is a curve showing light intensity of an assembled microLED probe driven different input voltages;

FIG. 13A is an energy dispersive X-ray spectrum that suggests $SiO_2$ residues are left at a boron-doped diamond/LED interface;

FIG. 13B is an image taken at a backside of a boron-doped diamond trace of a probe, showing surface morphology of the boron-doped diamond;

FIG. 14A are cyclic voltammetry (CV) curves of a flexible boron-doped diamond-parylene sensor for different concentrations of Ruhex in 1 M/L NaCl buffer solution, generated with a scan rate of 20 V/s and 10 cycles for each concentration;

FIG. 14B is a CV curve obtained from a commercially available boron-doped diamond sensor, which shows similar reduction-oxidation peak potentials as those shown in FIG. 13A;

FIG. 15 is a concept diagram of a flexible diamond sensor;

FIG. 16 is a graphic illustration of phases I-VIII of a device fabrication and boron-doped diamond transfer process;

FIG. 17A is a photograph showing a boron-doped diamond sensor fabricated according to various aspects of the current technology;

FIG. 17B is a photograph showing the device of FIG. 16A wrapped around a punch tip (3.5 mm in diameter), demonstrating the flexibility of the device;

FIG. 18A is a scanning electron microscope image showing a mesh structure and parylene anchors on a device fabricated according to various aspects of the current technology;

FIG. 18B is a Raman spectrum showing both boron and diamond peaks from a boron-doped diamond nucleation side of the device of FIG. 17A;

FIG. 18C is an energy dispersive X-ray spectrometry (EDS) image showing only a carbon peak, which implies no $SiO_2$ residue was detected;

FIG. 19A is a photograph that shows a transparent tape test where a boron-doped diamond (BDD)-parylene sensor fabricated according to various aspects of the current technology is attached to a piece of tape with the BDD side facing down onto the tape;

FIG. 19B is a photograph that shows the BDD-parylene sensor of FIG. 18A after it was peeled from the tape, wherein the BDD side is facing up in the photograph;

FIG. 20A shows voltammograms of an Au and boron-doped diamond (BDD) sensors in 1 mμ KCl versus Ag/AgCl, wherein the scan rates are 20 V/s for the BDD electrode and 0.1 V/s for the Au electrode;

FIG. 20B shows CV curves of the BDD sensor in various concentrations of $Ru(NH_3)_6^{2+/3+}$;

FIG. 20C is a fitting curve of cathodic peak current versus the concentrations of $Ru(NH_3)_6^{2+/3+}$;

FIG. 20D shows voltammograms of the BDD sensor in various concentrations of DA with a phosphate buffered saline (PBS) solution versus BDD, wherein the scan rates are 1 V/s;

FIG. 20E shows chronoamperograms of various concentrations of DA in PBS versus BDD at an applied potential of 1 V;

FIG. 20F is a fitting curve of background corrected current versus the concentrations of DA;

FIG. 21 is a graphic illustration of phases I-XIII of a device fabrication and boron-doped diamond transfer process;

FIG. 22A is photograph of a 3-electrode sensor made according to various aspects of the current technology, wherein the sensor is placed on a penny to provide scale;

FIG. 22B is photograph of a sensor probe made according to various aspects of the current technology, wherein the sensor probe is a in contact with a circuit board at a first end and with a penny at a second end;

FIG. 23A shows CV curves of dopamine (DA) and ascorbic acid (AA) generated from a sensor made according to the various aspects of the current technology, wherein the sensor was not modified and the DA and AA have similar oxidation peaks shown by arrow; and FIG. 23B shows CV curves of dopamine (DA) and ascorbic acid (AA) generated from a sensor made according to the various aspects of the current technology, wherein the sensor was modified to have an oxygen terminated BDD surface, and the DA and AA oxidation peaks are separated as shown by arrows.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges. As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B.

Example embodiments will now be described more fully with reference to the accompanying drawings.

The current technology provides a class of flexible, implantable sensors for applications in many fields, including, for example, biochemistry, medicine, and neural engineering. The sensors are made of hybrid polycrystalline-conductive material/polymer thin films, where the polycrystalline-conductive material is used as sensing elements and polymers are used as substrate and packaging materials. A wafer-level microfabrication method is developed to transfer large-scale conductive patterns onto mechanical flexible polymer substrates.

The polycrystalline-conductive material can be any flexible or hard and rigid conductive material known in the art that, such as highly doped semiconductor materials, such as silicon and GaAs, and boron doped polycrystalline diamond (BDD; which is hard and rigid) as non-limiting examples. For example, BDD exhibits a unique combination of properties, which makes it a suitable material for biological and chemical sensing, and implantable neural stimulation and recording devices. These properties include a high thermal conductivity, a low background current response, a large electrochemical potential window in aqueous solutions, chemical inertness, a high resistance to surface fouling, and biocompatibility. Therefore, other electrically conductive materials that demonstrate these characteristics and properties can also be used. BDD has been used for chemical sensing, such as for the detection of neurotransmitters, e.g., dopamine and serotonin. However, BDD is a hard and rigid material due to its high Young's modulus (about $10^{12}$ Pa). For specific applications, such as for implantable biosensors, a mechanical property mismatch between the rigid BDD and, for example, brain tissue (with a Young's modulus ranging from about $10^3$ to about $10^5$ Pa) can cause negative tissue responses, irritation, and/or irreversible damage. The same requirement applies to wearable sensors because a rigid material cannot have a conformal contact to skin, which causes deterioration of sensing performance over time.

Conventionally, BDD is synthesized at high temperatures (e.g., 500° C. to 900° C.) on temperature insensitive, solid substrates, such as metals and silicon. These high temperature synthesis conditions do not allow BDD to be grown directly onto mechanically flexible polymers, which typically have melting points below the high temperatures required to synthesize BDD. Alternative fabrication methods have been implemented to combine small scale BDD with a flexible polymer, such as for the construction of diamond-on-polymer electrode arrays constructed by transferring selectively grown diamond electrodes onto a spin-coated polynorbornene-based polymer. Also, flexible diamond microelectrode arrays have been constructed by coating selectively grown diamond with polyimide and releasing the polyimide from a substrate. However, these methods only allow for transferring small diamond microelectrodes from silicon wafers. In contrast, the current technology provides for transferring large-scale, all-diamond patterns from rigid metal/silicon substrates to mechanically flexible polymer thin films.

The fabrication method provided herein makes it possible to transfer large-scale, patterned devices, such as all-diamond devices, including microelectrodes, interconnects, and contact pads, from a silicon wafer to a flexible substrate. The flexible substrate can be any polymeric material known in the art capable of being deposited by chemical vapor deposition (CVD), such as poly(ethylene terephlate) (PET), poly(styrene) (PS), poly(p-xylylene) polymers, and conductive polymers, such as polypyrrole, as non-limiting examples. For example, parylene-C (a poly(p-xylylene polymer) is a biocompatible, transparent, flexible, room-temperature-deposited polymer, which provides moisture and dielectric barriers for implanted devices. Also, parylene-C has a Young's modulus (about $10^9$ Pa) closer to tissue and has been used as a structural and packaging polymer for implantable devices. Therefore, other flexible substrate materials that provide these properties and characteristics can be used.

Figure 1:
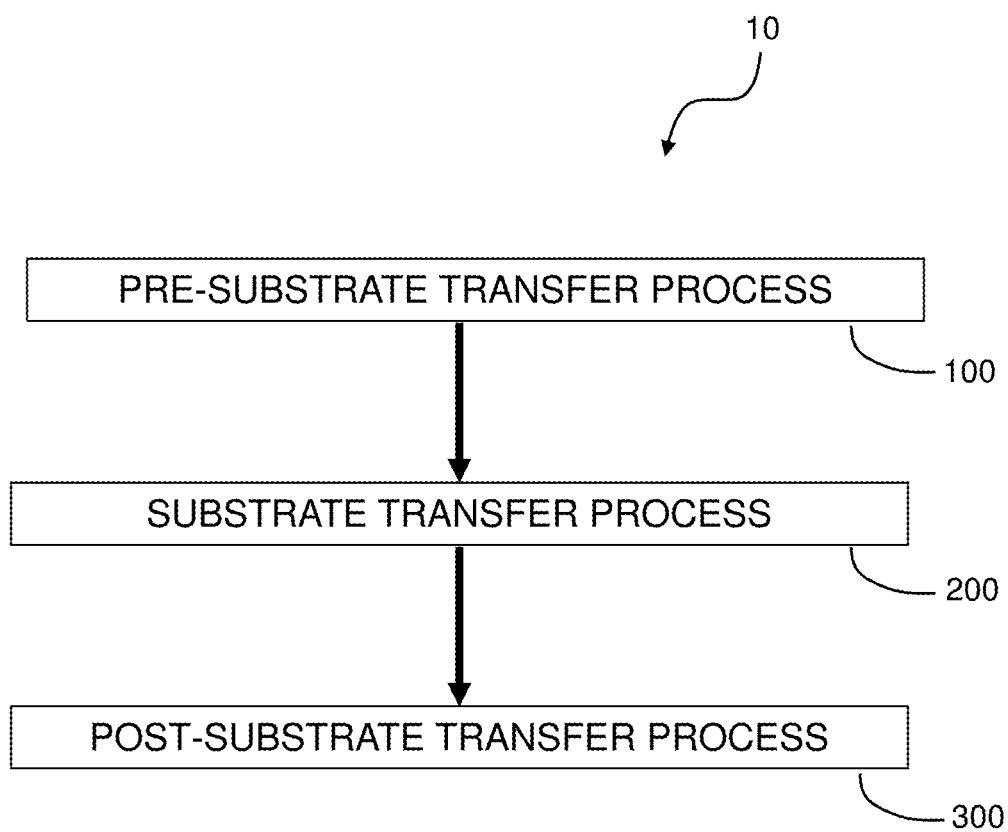
FIG. 1 is a block diagram providing a method for fabricating a device according to various aspects of the current technology.
Figure 2A:
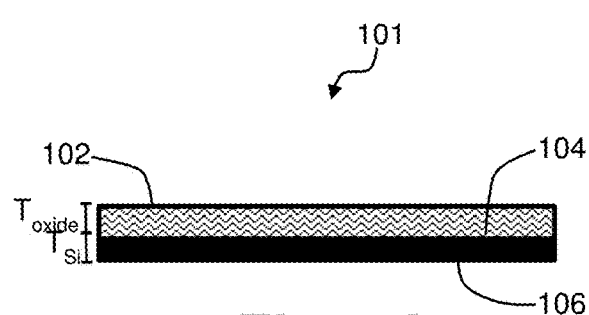
FIG. 2A is a cross-sectional illustration of a device during a first phase of a pre-substrate transfer process.

FIG. 1 provides a method 10 for fabricating a device according to the current technology. In block 100, the method includes a pre-substrate transfer process. FIGS. 2A-2D provide cross-sectional illustrations of such a device 101 that demonstrate the pre-substrate transfer process provided in block 100. In FIG. 2A the pre-substrate transfer process includes generating a layer of $SiO_2$ 102 on a first surface 104 of a Substrate 106. The substrate 106 can comprise any material known in the art, such as for example, silicon (Si), glass, or GaAs. In various embodiments, the substrate 106 is a Si wafer. In various embodiments, the substrate 106 has a thickness $T_{Si}$ of from about 50 μm to about 1 mm, from about 100 μm to about 800 μm, from about 200 μm to about 600 μm, or from about 300 μm to about 500 μm. The layer of $SiO_2$ 102 is generated by any method known in the art, such as by, for example, plasma enhanced chemical vapor deposition (PECVD) or by thermal oxidation. In various embodiments, layer of $SiO_2$ 102 has a thickness $T_{oxide}$ of from about 0.25 μm to about 5 μm, from about 0.5 μm to about 3 μm, or from about 1 μm to about 2 μm.

Figure 2C:
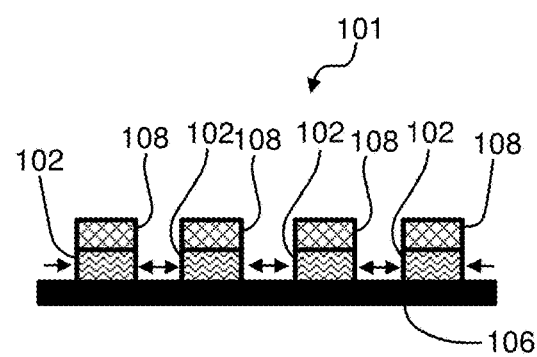
FIG. 2C is a cross-sectional illustration of the device during a third phase of the pre-substrate transfer process of FIG. 2A.
Figure 2B:
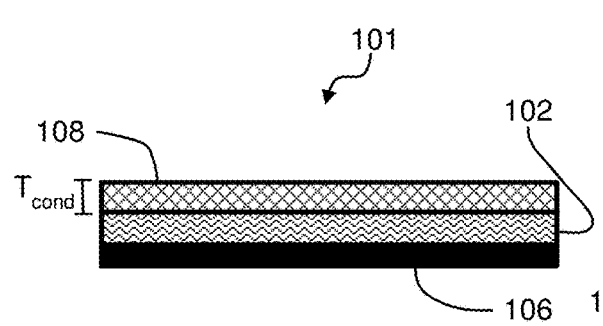
FIG. 2B is a cross-sectional illustration of the device during a second phase of the pre-substrate transfer process of FIG. 2A.

After the layer of $SiO_2$ 102 is generated on the substrate 106, the pre-substrate transfer process includes, in FIG. 2B, disposing layer of an electrically conductive material 108 on the layer of $SiO_2$ 102. The electrically conductive material 108 can be any hard and rigid electrically conductive material described above, including BDD. In various embodiments, the layer of the electrically conductive material 108 has a thickness $T_{cond}$ of from about 0.25 μm to about 10 μm, from about 0.5 μm to about 8 μm, from about 1 μm to about 5 μm, or from about 2 μm to about 3 μm. Although the layer of electrically conductive material 108 may be made thicker than 10 μm, this comes with increased device rigidity and a loss of device flexibility. However, the device 101 may be scaled up to have a larger surface area without sacrificing flexibility.

In FIG. 2C, the method includes removing a portion, i.e., patterning, of the electrically conductive material 108 to provide a pattern of the electrically conductive material 108 on the layer of $SiO_2$ 102. Patterning a portion of the electrically conductive material 108 can be performed by any method known in the art, such as, for example, by photolithography, laser ablation or chemical etching. In some embodiments, removing a portion of the electrically conductive material 108 comprises disposing a metal layer of aluminum (Al), gold (Au) or copper (Cu) (having a thickness of from about 0.25 μm to about 2 μm, or from about 0.5 μm to about 1.5 μm, such as a thickness, for example, of about 0.5 μm, 0.75 μm, 1 μm, 1.5 μm, 1.75 μm, or 2 μm) on the layer of the electrically conductive material 108, disposing a layer of a photoresist on the layer of aluminum, such as, for example, by spin coating, and disposing an ultraviolet light (UV)-transparent mask comprising the pattern or plurality of patterns over the layer of photoresist, wherein the pattern is not transparent to UV light. These layers are then exposed to ultraviolet (UV) light to transfer the pattern or plurality of patterns onto the layer of photoresist. The device 101 is then subjected to plasma or chemical etching, which etches and transfers the pattern or patterns provided by the mask into the layer of an electrically conductive material 108 and the layer of $SiO_2$ 102. Chemical etching is performed with aluminum etchant (such as Type A aluminum etchant from Transene, Inc., Danvers, Mass.), hydrofluoric acid (HF) diluted to from about 1% to about 20% or from about 5% to about 10% in water, P-etch (described below), or buffer oxide etch (BOE, described below). However, it is understood that a lift-off process can also be used to transfer a pattern into the electrically conductive material 108. By way of a non-limiting example, the lift-off process can include disposing a layer of photoresist, such as by, for example, spin coating, onto the layer of electrically conductive material 108 and disposing a transparent mask comprising a negative pattern onto the layer of photoresist. Exposing the mask and photoresist to UV light transfers the negative pattern in to the photoresist. A layer comprising aluminum (Al), gold (Au), or copper (Cu) is then disposed over the patterned photoresist. Contact with photoresist remover dissolves the photoresist, which carries the layer of Al, Au, or Cu with it, such that the Al, Au, or Cu will remain on areas where there is no photoresist. The photoresist remover can be an organic solvent, such as acetone, or an alkaline solution, such as photoresist developer, as non-limiting examples. The device 101 is then subjected to plasma or chemical etching as described above.

The pattern or plurality of patterns in the mask is predetermined and may individually include a single interconnected pattern or a plurality of unconnected segments that collectively comprise the pattern. For example, the mask may include a pattern including at least one of a working electrode (WE), a counter electrode (CE), and a reference electrode (RE), where the electrodes do not make physical contact with another segment of the pattern. In contrast, the pattern may include a plurality of features that are interconnected. The plurality of features may include microelectrodes, interconnects, contact pads, and combinations therefore, as non-limiting examples. Therefore, the pattern is not limiting except with regard to aperture-providing features described herein. Moreover, when a plurality of individual patterns is provided on a mask, the plurality of individual patterns may be the same pattern or different patterns. Each pattern may have a width of from about 0.5 mm to about 10 mm, or greater than 10 mm as long as the pattern fits entirely on the substrate 106. Similarly, each pattern may have a length of from about 0.5 mm to about 10 mm, or greater than 10 mm as long as the pattern fits entirely on the substrate 106. Individual segments of the pattern may have widths of from about 1 μm to about 10 mm or larger.

As described above, the pattern or patterns in the mask are transferred to the layer of the electrically conductive material 108. The individual pattern or patterns include at least one feature, including a plurality of features, that transfers at least one aperture, including a plurality of apertures, i.e., a mesh, to the electrically conductive material 108, such that the at least one aperture extends through the electrically conductive material 108, through the layer of $SiO_2$ 102, and optionally to the substrate 106. Each aperture has a diameter (or length in at least one dimension) of from about 10 μm to about 200 μm, from about 15 μm to about 100 μm, or from about 20 μm to about 50 μm. The at least one aperture can have any cross sectional geometry, such as a circle, square, rectangle, diamond, star, triangle, and trapezoid, as non-limiting examples. As described below, the at least one aperture is necessary for the formation of an undercut and/or anchor that is used to adhere the electrically conductive material 108 to a flexible polymeric material.

Figure 2D:
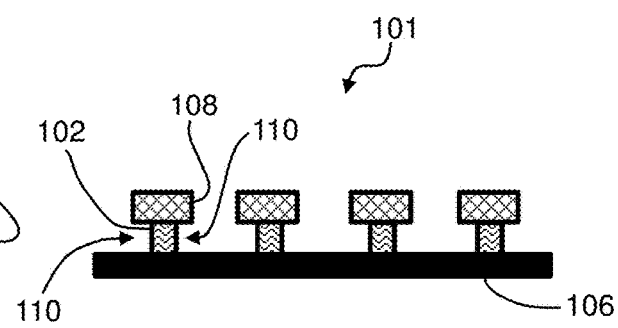
FIG. 2D is a cross-sectional illustration of the device during a fourth phase of the pre-substrate transfer process of FIG. 2A.

As shown in FIGS. 2C and 2D, after a pattern has been transferred to the electrically conductive material 108 and optionally to the layer of $SiO_2$ 102, the $SiO_2$ in the layer of $SiO_2$ 102 is partially removed. Accordingly, the method includes applying an etching compound into the apertures to etch the $SiO_2$ vertically downward to the substrate 106 if necessary and to over etch in horizontal directions (as shown by the horizontal arrows in FIG. 2C) beneath the electrically conductive material 108, such that a portion of the $SiO_2$ beneath the electrically conductive material is removed to form undercuts 110. The etching compound can be any etching compound used in the art, such as, hydrofluoric acid (about 1% to about 20% or from about 5% to about 10% in water), P-etch and buffered oxide etch (BOE), as non-limiting examples. P-etch includes about 60 volumes of $H_2O$, about 3 volumes of HF, and about 2 volumes of $HNO_3$. BOE includes a buffering agent, ammonium fluoride (NH4F), and hydrofluoric acid (HF). In one embodiment, the BOE includes about 6 volumes of ammonium fluoride (NH4F, 40% solution) and about 1 volume of HF (49%). The BOE etches $SiO_2$ horizontally at a horizontal etching rate of from about 1000 Å/min to about 2500 Å/min. Therefore, the size of the undercuts 110 can be controlled by allowing the BOE to etch the $SiO_2$ for a predetermined amount of time based on the horizontal etching rate. Based on the desired size of undercuts 110, which may be from about 1 μm to about 10 μm or from about 1 μm to about 5 μm, the etching compound may be applied for from about 1 min to about 10 min or from about 1 min to about 5 min. However, it is understood that longer periods of time may be necessary depending on the size of the undercuts 110 desired.

Figure 3A:
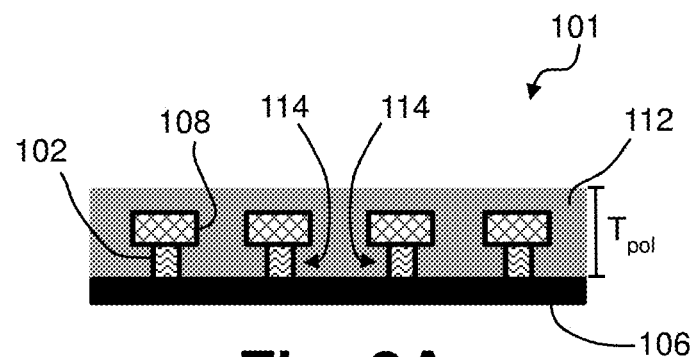
FIG. 3A is a cross-sectional illustration of a device during a first phase of a substrate transfer process.
Figure 3B:
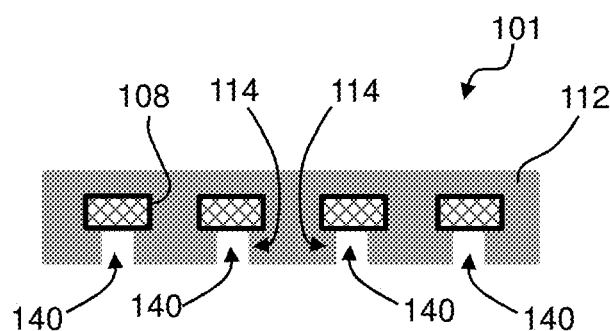
FIG. 3B is a cross-sectional illustration of the device during a second phase of the substrate transfer process of FIG. 3A.
Figure 3C:
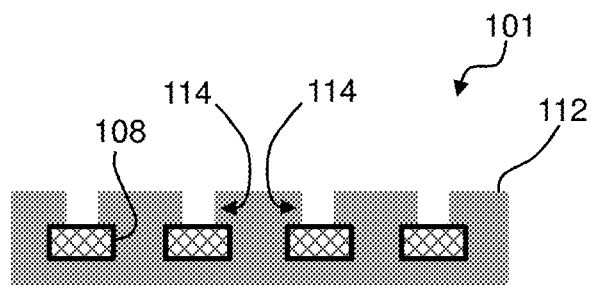
FIG. 3C is a cross-sectional illustration of the device during a third phase of the substrate transfer process of FIG. 3A.

With reference to FIG. 1, in block 200 the method 10 for fabricating a device includes a substrate transfer process. FIGS. 3A-3C provide cross-sectional illustrations that demonstrate the substrate transfer process provided in block 200. In FIG. 3A the substrate transfer process includes disposing a flexible polymeric material 112 over the electrically conductive material 108, such that the flexible polymeric material 112 conformingly coats the electrically conductive material 108, such that the flexible polymeric material 112 fills the undercuts 110 and covers the electrically conductive material 108. The flexible polymeric material 112, which can be any flexible polymeric material discussed herein, including, for example, parylene-C, is disposed by chemical vapor deposition (CVD). Via this process, the flexible polymeric material 112 gets disposed under the undercuts 110 to form anchors 114, which hold the electrically conductive material 108 to the flexible polymeric material 112. After disposing the flexible polymeric material 112, the flexible polymeric material 112 has a thickness $T_{pol}$ of greater than or equal to about 1 μm, greater than or equal to about 3 μm, greater than or equal to about 5 μm or greater than or equal to about 10 μm. For example, the flexible polymeric material 112 may have a thickness $T_{pol}$ of from about 1 μm to about 50 μm, of from about 3 μm to about 20 μm, or from about 5 m to about 10 μm. Although thicker layers of flexible polymeric material 112 are possible, the device 101 becomes more rigid as the thickness increases.

Optionally, prior to disposing the flexible polymeric material 112, the device 101, including the first surface 104 of the substrate 106, the layer of $SiO_2$ 102, and the electrically conductive material 108, can be treated with an adhesion promoter to further promote adhering or coupling the flexible polymeric material 112 to the electrically conductive material 108. A non-limiting example of an adhesion promoter is silane A174 (γ-methacryloxypropyltrimethoxysilane).

With reference to FIG. 3B, the substrate transfer process described in block 200 of FIG. 1 includes removing the Substrate 106 and the remainder of the $SiO_2$ by etching to thereby release the flexible polymeric compound 112 including the electrically conducting material 108. Here, etching can be performed by chemical etching or by dry plasma etching. For example, chemical etching of $SiO_2$ can performed with diluted hydrofluoric acid (about 1% to about 20% or from about 5% to about 10% in water), and plasma dry etching of $SiO_2$ can be conducted in a reactive ion etcher (RIE) or inductively coupled plasma RIE (ICP-RIE) using fluorine-containing gases, such as $SF_6$, $CF_4$, $CHF_3$, or a mixture of at least two of $SF_6$, $CF_4$ (gas), $CHF_3$ (gas), and He (gas), as non-limiting examples. After etching, the electrically conductive material 108 is partially exposed to the atmosphere at regions between the anchors 140.

In various embodiments, chemical etching is performed by contacting a chemical etchant, such as potassium hydroxide (KOH), tetramethylammonium hydroxide (TMAH), or HF/nitric/acetic acid (HNA), as non-limiting examples, to the substrate 106 and the $SiO_2$ after the substrate 106 is removed. For example, KOH at a concentration of from about 30% to about 35% provides an etching rate of about 1 μm/min, TMAH at a concentration of about 25% provides an etching rate of about 0.6 μm/min, and HNA with a formulation of from about 2 to about 3 volumes HF, from about 2 to about 3 volumes of nitric acid, and about 5 volumes of acetic acid, provides an etching rate of from about 3 μm/min to about 5 μm/min.

Figure 4:
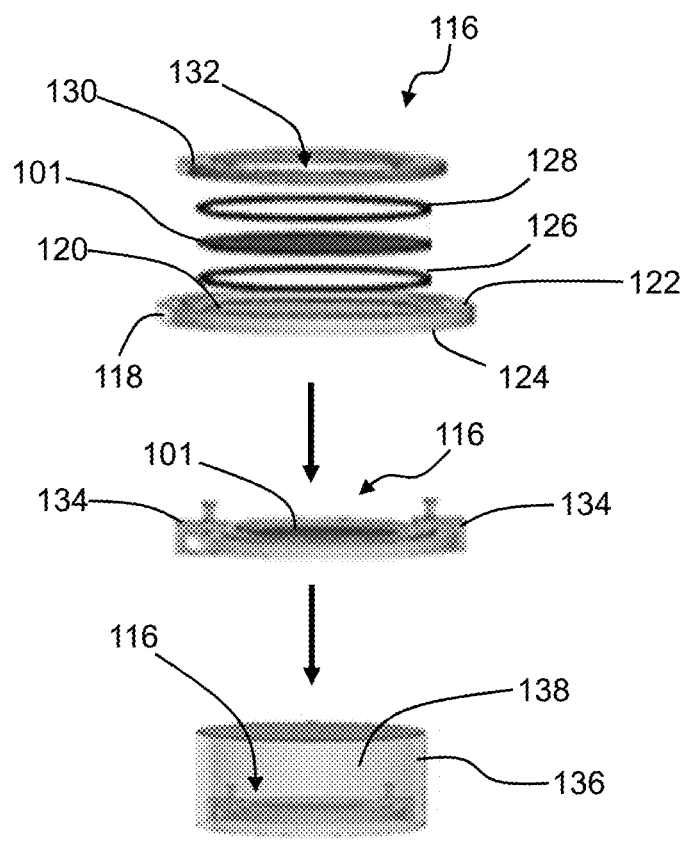
FIG. 4 is an illustration of an etching jig.

In order to facilitate the chemical etching process, the device 101 including the substrate 106, the layer of $SiO_2$ 102, and the electrically conductive material 108 may be transferred to a jig. FIG. 4 shows an illustration of a jig 116 that can be used to facilitate chemical etching. The jig 116 includes a cylindrical housing 118 having a first surface 120 with an elevated rim 122 that extends along an edge of the housing 118. The housing 118 and the rim 122 have a shape that matches the substrate 106. For example, when the substrate 106 is a circular Si wafer, the housing 118 and associated rim 122 are circular such that the Si wafer will fit on the housing 118 and within the rim 122. The housing 118 also includes a second opposing surface 124, which is solid. The jig 116 also includes a first O-ring 126, a second O-ring 128, and an annular cap 130 with a central circular opening 132. To assemble the jig 116, the first O-ring is positioned on the first surface 120 of the housing 118, such that the rim 122 extends about the first O-ring 126. The device 101 is then positioned on top of the first O-ring 126 with the flexible polymeric material 112 facing downward toward the first surface 120 of the housing 118 and with the substrate 106 facing upward. Next, the second O-ring 128 is positioned on the device 101 (on the substrate 106 portion) and the annular cap 132 is positioned on the second O-ring 128. The Si substrate associated with the electrically conductive material 108 is exposed to the environment through the second O-ring 128 and through the opening 132 of the annular cap 130. Clamps 134 hold the jig 116 together with the device 101 immobilized between the O-rings 126, 128, such that, when the jig 116 is exposed to a solution, only the portion of the device 101 facing upward, i.e., the substrate 106, is exposed to the solution. Therefore, the jig 116 is transferred to a container 136 containing a liquid chemical etchant 138, such as KOH, TMAH, or HNA, for a period of time sufficient to remove the Si substrate.

Dry plasma etching may also be used to remove the substrate 106 and $SiO_2$ from the device 101. Dry plasma etching comprises binding a surface of the device 101 including the flexible polymeric material 112 to a carrier substrate using a bonding agent, such as, for example, polyphenyl ether. The substrate 106, which is left exposed, is etched from the device 101 using, as non-limiting examples, deep-reactive ion dry etching (DRIE), plasma etching, reactive ion etching (RIE), inductively coupled plasma reactive ion etching (ICP-RIE), or Xenon Difluoride (XeF2).

As shown in FIG. 3C, after removing the substrate 106 and the remainder of the $SiO_2$ by etching, the device 101 may be inverted, such that the surface of the electrically conducting material 106 exposed to the atmosphere is facing upward to make processing of the device 101 easier.

Figure 5:
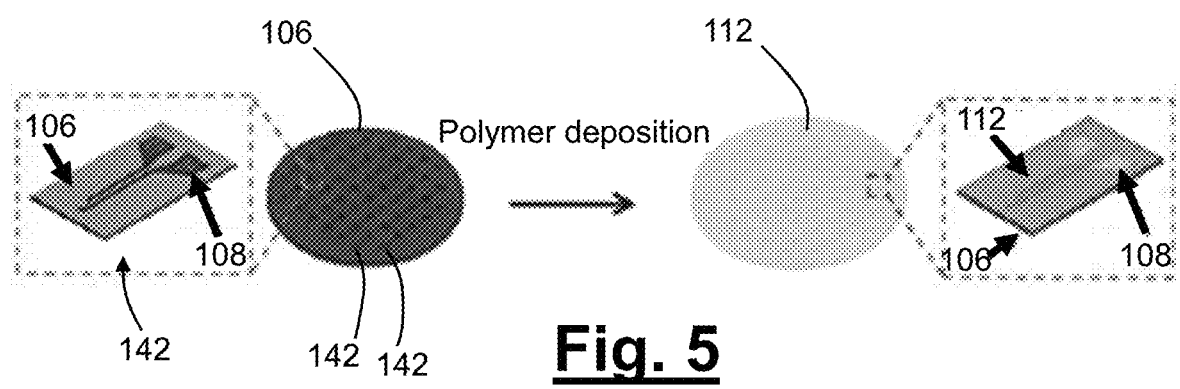
FIG. 5 is a graphic illustration of a pre-substrate transfer process and a portion of a substrate transfer process.

FIG. 5 provides an illustration of the pre-substrate transfer process and a portion of the substrate transfer process. The pre-substrate transfer process generally includes disposing or patterning the conductive material 106 onto the substrate 106 as a predetermined pattern, and coating the conductive material with a flexible polymer 112. As shown in FIG. 5, a plurality of predetermined patterns 142 of the conductive material 108 comprising at least one aperture are disposed or patterned onto the substrate 106, which may be a Si wafer. The plurality of predetermined patterns 142 may all be the same pattern or a variety of patterns. After the predetermined pattern or plurality of predetermined patterns 142 are disposed on the substrate 106, the predetermined pattern or plurality of predetermined patterns 142 are coated with a flexible polymer 106, which flows through the apertures to generate the anchors (see anchors 114 in FIG. 3A). As shown in FIG. 5, the electrically conductive material 106 is optically visible through the flexible polymeric material 112.

Figure 6A:
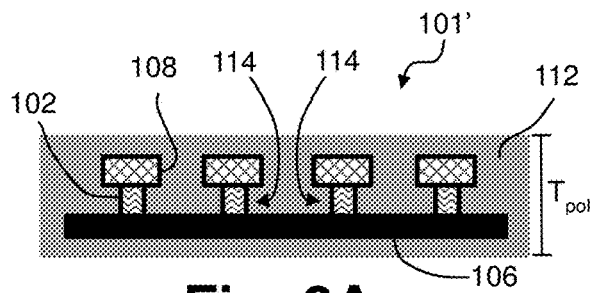
FIG. 6A is a cross-sectional illustration of a device during a first phase of a second substrate transfer process.

FIGS. 6A-6I provide cross-sectional illustrations that demonstrate a variation of the substrate transfer process provided in block 200 of FIG. 1 with respect to a device 101'. When layers or materials are in common with the process shown in FIGS. 3A-3C, reference numerals are maintained. In FIG. 6A the substrate transfer process includes disposing a flexible polymeric material 112 over the electrically conductive material 108, such that the flexible polymeric material 112 conformingly coats the electrically conductive material 108. The flexible polymeric material 112 fills the undercuts 110 (see FIG. 2D) and covers the entire device 101', including the electrically conductive material 108. The flexible polymeric material 112 can be any flexible polymeric material described above. Via this process, the flexible polymeric material 112 gets disposed under the undercuts 110 to form anchors 114, which hold the electrically conductive material 108 to the flexible polymeric material 112. The flexible polymeric material 112 has a thickness $T_{pol}$ of greater than or equal to about 1 µm, greater than or equal to about 3 µm, greater than or equal to about 5 µm or greater than or equal to about 10 µm. For example, the flexible polymeric material 112 may have a thickness $T_{pol}$ of from about 1 µm to about 50 µm, of from about 3 µm to about 20 µm, or from about 5 m to about 10 µm. Although thicker layers of flexible polymeric material 112 are possible, the device 101' becomes more rigid as the thickness increases.

Figure 6F:
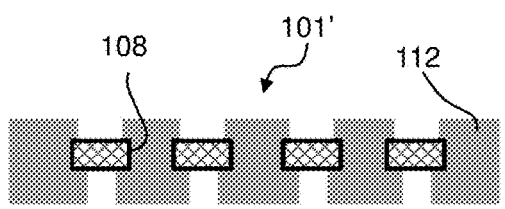
FIG. 6F is a cross-sectional illustration of a device during a sixth phase of a second substrate transfer process.
Figure 6B:
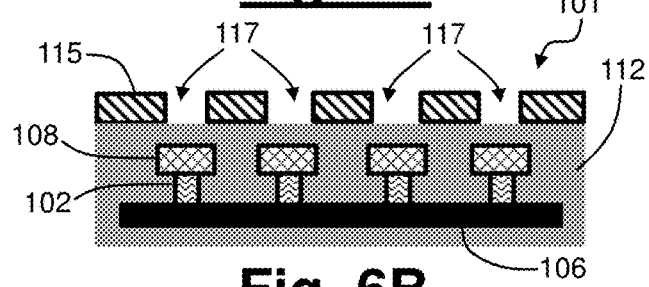
FIG. 6B is a cross-sectional illustration of a device during a second phase of a second substrate transfer process.
Figure 6G:
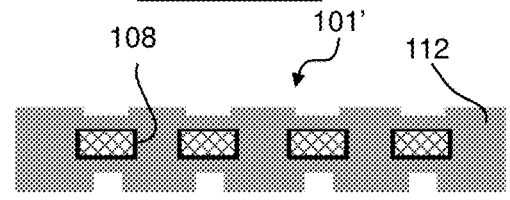
FIG. 6G is a cross-sectional illustration of a device during a seventh phase of a second substrate transfer process.
Figure 6C:
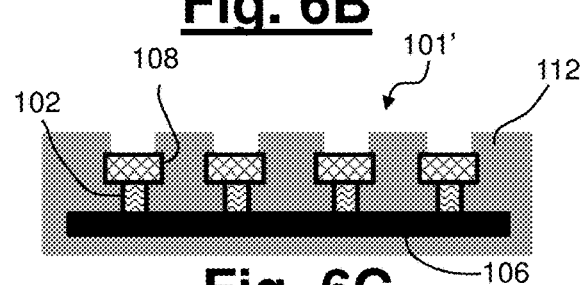
FIG. 6C is a cross-sectional illustration of a device during a third phase of a second substrate transfer process.

In FIG. 6B, the process includes disposing a mask 115 comprising titanium, copper, or a combination thereof to a surface of the flexible polymeric material 112. The mask includes voids or apertures 117 in locations above the electrically conductive material 108. Then if FIG. 6C, the process includes etching the flexible polymeric material 112 to expose the electrically conductive material 108. By way of non-limiting examples, etching is performed by plasma dry etching, for example, with oxygen ($O_2$) as a reaction gas or by laser patterning using, for example, a KrF excimer laser operating at about 248 nm with a pulse duration of about 20 ns, wherein the ablation threshold for parylene at 10 pulses is about 340 $mJ/cm^2$.

Figure 6H:
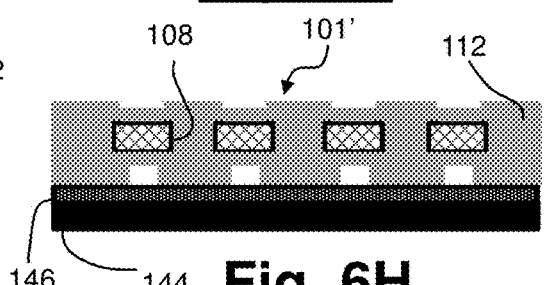
FIG. 6H is a cross-sectional illustration of a device during a eighth phase of a second substrate transfer process.
Figure 6D:
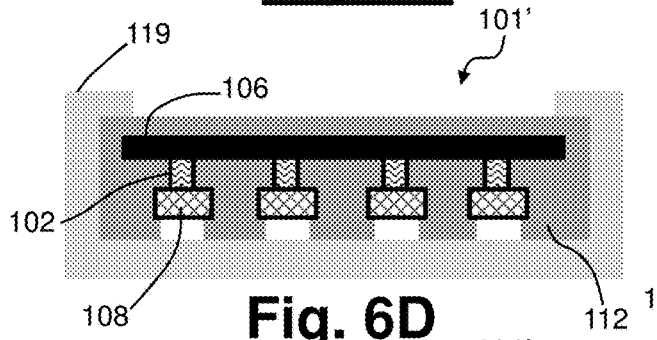
FIG. 6D is a cross-sectional illustration of a device during a fourth phase of a second substrate transfer process.
Figure 6I:
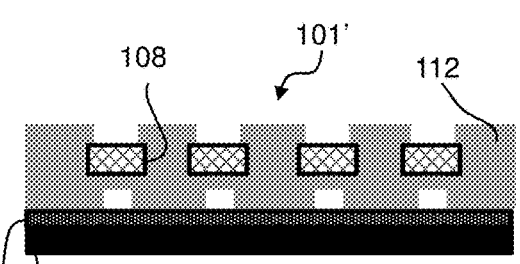
FIG. 6I is a cross-sectional illustration of a device during a first ninth phase of a second substrate transfer process.
Figure 6E:
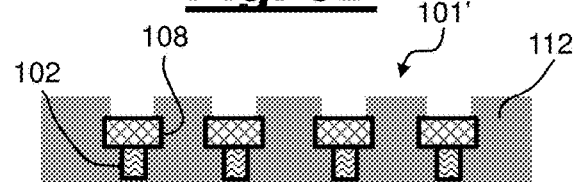
FIG. 6E is a cross-sectional illustration of a device during a fifth phase of a second substrate transfer process.

In FIG. 6D, the process includes disposing the device 101' into a jig 119, such as the jig described above, with the electrically conductive material 108 facing down and the flexible polymeric material 112 facing upward and exposed. In FIG. 6E the process includes removing a portion of the flexible polymeric material 112 and the substantially all of the substrate 106 by chemical etching or by dry plasma etching as described above in regard to FIG. 3B. As used herein, the term "substantially all of the substrate" means at least 80% of the substrate is removed, and in some embodiments, at least 85%, at least 90%, at least 95%, or at least 98% of the substrate is removed. After substantially all of the substrate 106 has been removed, the device 101' is removed from the jig 119 as shown in FIG. 6E.

In FIG. 6F, the process includes removing the layer of $SiO_2$ 102, such as for example, by chemical or dry plasma etching. As non-limiting examples, chemical etching includes contacting the layer of $SiO_2$ with a hydrofluoric acid (HF) solution (from about 1% to about 20%, HF in water), P-etch, or BOE, and plasma etching includes plasma of fluorine containing gases, such as, for example, $SF_6$, $CF_4$, $CHF_3$, or a mixture of at least two of $SF_6$, $CF_4$ (gas), $CHF_3$ (gas), and He (gas). Removing the $SiO_2$ 102 thereby exposes the electrically conductive material 108. Then in FIG. 6G, additional flexible polymeric material 112 is disposed over the electrically conductive material 108. In some embodiments, one side of the device 101' is covered or protected, such that only an opposing exposed uncovered or unprotected side receives the flexible polymeric material 112 over the electrically conductive material 108. In such embodiments, the substrate transfer process ends at this point.

Figure 6J:
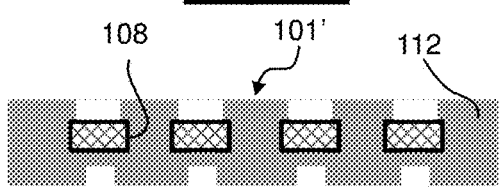
FIG. 6J is a cross-sectional illustration of a device during a tenth phase of a second substrate transfer process.

In FIG. 6H, the process includes optionally attaching a carrier substrate 144 to the device 101' by way of photoresist 146. The carrier substrate 144, which may be, for example, a silicon wafer, makes the device 101' easier to manipulate. Then in FIG. 6I, the process includes removing exposed flexible polymeric material 112 that is located above the electrically conductive material 108, by any method described above. When the optional carrier substrate 144 is utilized, it is then removed in FIG. 6J. The result is a device 101' comprising a pattern of electrically conductive material 108 embedded within the flexible polymeric material 112 by way of anchors 114.

In various embodiments, at least a portion of the electrically conductive material 108 is modified. Modifying at least a portion of the electrically conductive material 108 includes, for example, chemically modifying at least a portion of the electrically conductive material 108, disposing a ligand to at least a portion of the electrically conductive material 108, or applying a thin film to at least a portion of the electrically conductive material 108. Therefore, the method can include at least one of chemically modifying at least a portion of the electrically conductive material 108, disposing a ligand to at least a portion of the electrically conductive material 108, or disposing a thin film over at last a portion of the electrically conductive material 108. Chemical modification includes oxygen terminating at least a portion of the electrically conductive material 108 by placing the device 101, 101' in a KOH solution, applying an electrical potential between various portions of the electrically conductive material 108. Chemical modification also includes plasma treatments or disposing ozone to at least a portion of the electrically conductive material 108. Ligand modification includes disposing small molecules, large molecules, bio-molecules, or a combination thereof to at least a portion of the electrically conductive material 108, wherein bio-molecules include peptides, proteins (including, for example, growth factors), protein fragments, immunoglobulins, immunoglobulin fractions, DNA molecules, RNA molecules, or combinations thereof. Thin film modification includes applying nanoparticles, polymers and copolymers, such as, for example, gold nanoparticles and/or Nafion, to at least a portion of the electrically conductive material 108. In various embodiments, the electrically conductive material 108 defines at least one electrode and at least one of the at least one electrode is modified. For example, the electrically conductive material 108 can define a working electrode, a counter electrode, and a reference electrode, wherein at least the working electrode is modified.

Figure 7A:
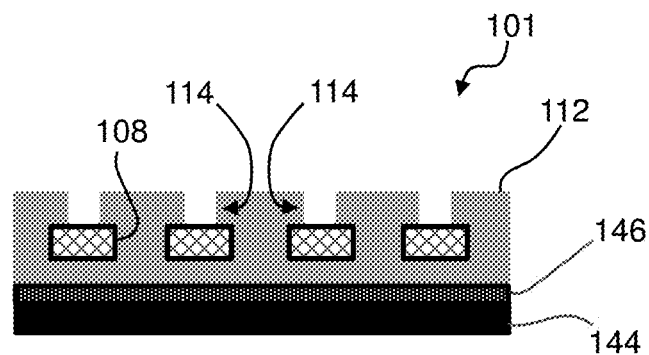
FIG. 7A is a cross-sectional illustration of a device during a first phase of a post-transfer substrate transfer process.
Figure 7B:
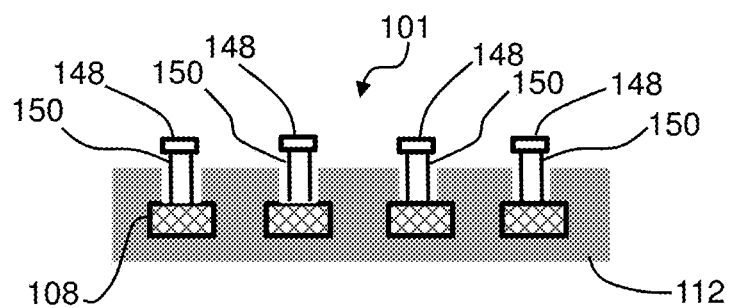
FIG. 7B is a cross-sectional illustration of the device during a second phase of the post-transfer substrate transfer process of FIG. 6A.

With reference to FIG. 1, in block 300 the method 10 for fabricating a device includes an optional post-substrate transfer process. FIGS. 7A and 7B provide cross-sectional illustrations that demonstrate the post-substrate transfer process provided in block 300, continuing from either FIG. 3C or FIG. 6J (or in some embodiments from FIG. 6G). In FIG. 7A, the post-substrate transfer process optionally includes attaching a carrier substrate (or carrier wafer) 144 to the flexible polymeric material 112 with photoresist 146. Attaching the carrier substrate 144 to the device 101 makes handling the device 101 easier during the post-substrate transfer process relative to if no carrier substrate was used.

Figure 7C:
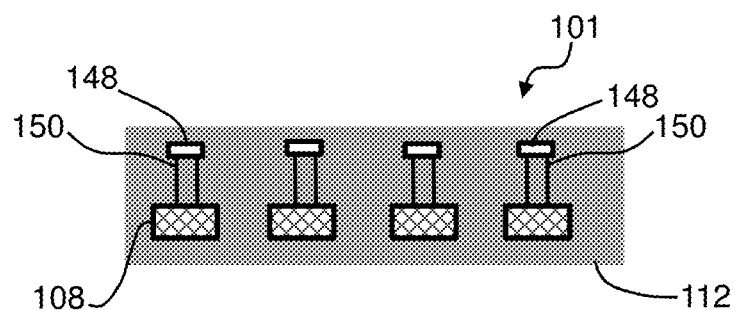
FIG. 7C is a cross-sectional illustration of a device during a third phase of the post-transfer substrate transfer process of FIG. 6A.
Figure 8:
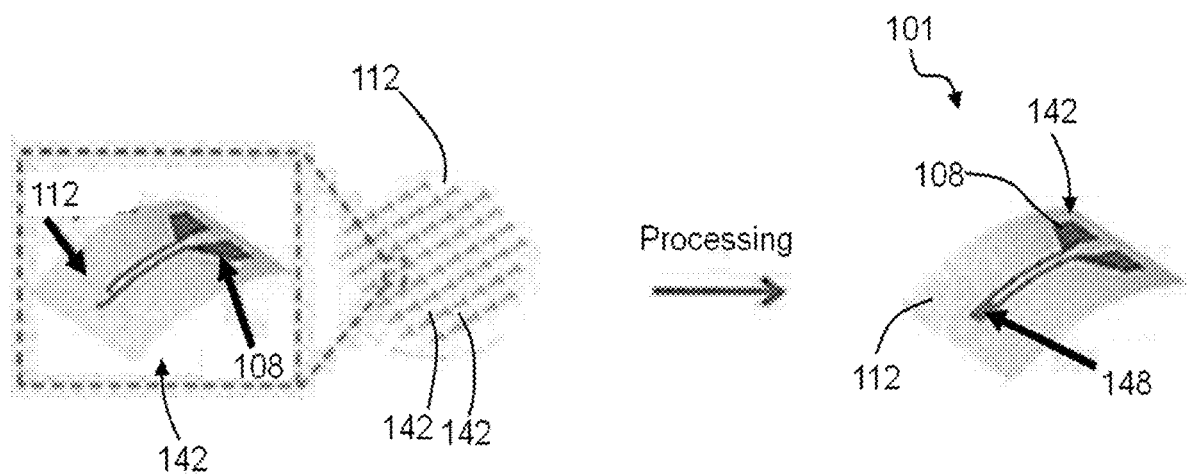
FIG. 8 is a graphic illustration of a post-substrate transfer process.

In FIG. 7B, the post-substrate transfer process includes attaching components to the electrically conducting material 108, which is coupled to the flexible polymer material 112 with at least the anchors 114. The components may include contact pads, contacts, light emitting diodes (LEDs), micro LEDs (pLEDs), wires, and combinations thereof as non-limiting examples. In FIG. 7B, pLEDs 148 are connected to the electrically conductive material 108 by contact pads 150. The components may be coupled to the electrically conducting material 108 by any means known in the art, such as by evaporation, soldering, and self-assembly, as non-limiting examples. After the components are attached to the device 101, carrier substrate 144 and photoresist 146 may be removed by dissolving the photoresist in, for example, an organic solvent, such as acetone. Optionally, the device may be encapsulated with the flexible polymeric material 112, as shown in FIG. 7C. Next, the completed devices 101 may be individually cut out from the flexible polymeric material 112 with, for example, a laser, scissors, or other suitable cutting device. When included, the carrier substrate 144 can be removed, for example, prior to the cutting.

Fig. provides an illustration of the post-substrate transfer process. The post-substrate transfer process generally includes optionally coupling the device 101 to a carrier substrate 144 and attaching components, such as a pLED 148 to the pattern 142 of electrically conductive material 108. Individual devices 101 are then cut out of the flexible polymeric material to yield completed devices, which are flexible and suitable for implantation into biological tissues.

Figure 9:
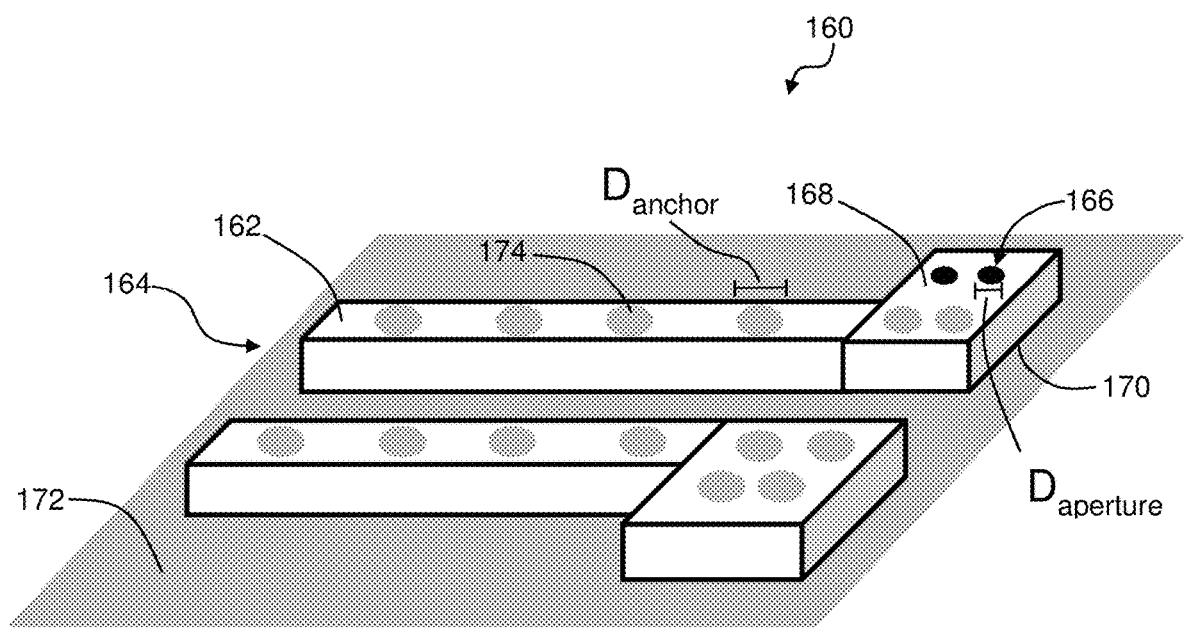
FIG. 9 is a graphic illustration of a device according to various aspects of the current technology.

The current technology also provides an implantable device generated by the methods described herein. An exemplary implantable device 160 is shown in FIG. 9. The implantable device 160 comprises an electrically conductive material 162 that defines a predetermined pattern 164, wherein the pattern includes at least one aperture 166 that extends from a first top surface 168 of the electrically conductive material 162 to a second bottom opposing surface 170 of the electrically conductive material 162. The apertures 166 can have any cross sectional geometry, such as a circle, square, rectangle, diamond, star, triangle, and trapezoid, as non-limiting examples.

The device 160 also includes a flexible polymeric substrate 172 attached to the bottom surface 170 of the electrically conductive material 162. Therefore, the second surface 170 of the electrically conductive material 162 is disposed on the flexible polymeric substrate 172. The flexible polymeric substrate 172 unitarily and monolithically extends through the at least one aperture 166 from the second surface 170 to the first surface 168 and extends radially on the first surface 168 about the aperture 166 to form anchors 174 that partially cover the electrically conductive material 162 and hold the electrically conductive material 162 against the flexible polymeric substrate 172. The apertures 166 are shown without anchors 174 solely for the purpose of illustration. Accordingly, the anchors 174 have a diameter $D_{anchor}$ that is larger than a diameter $D_{aperture}$ of the apertures 166. Optionally, the flexible polymeric substrate 172 encapsulated the pattern 164 of electrically conductive material 162 in addition to providing the anchors 174.

The device 160 may also include components, such as described above, i.e., contact pads, contacts, light emitting diodes (LEDs), micro LEDs (pLEDs), and wires, as non-limiting examples (not shown in FIG. 9). The electrically conductive material 162 and flexible polymeric substrate can be composed of any corresponding materials described herein. In FIG. 9, two apertures 166 are shown without the flexible polymeric substrate 172 extending therethrough for the purpose of depicting the apertures 166, which are generally covered by the anchors 174.

In various embodiments, the device 160 is an implantable probe or sensor having a Young's modulus that is closer to the Young's modulus of a mammalian brain, relative to the Young's modulus of BDD, wherein the mammalian brain is a brain of a human, a non-human primate, a horse, a cow, a mouse, a rat, a dog, or a cat, as non-limiting examples.

Embodiments of the present technology are further illustrated through the following non-limiting examples.

Example 1

Two devices made by hybrid diamond-parylene thin films, including an optrode probe for optical stimulation and neural recording and a microscale sensor for chemical detection are provided here.

Figure 10A:
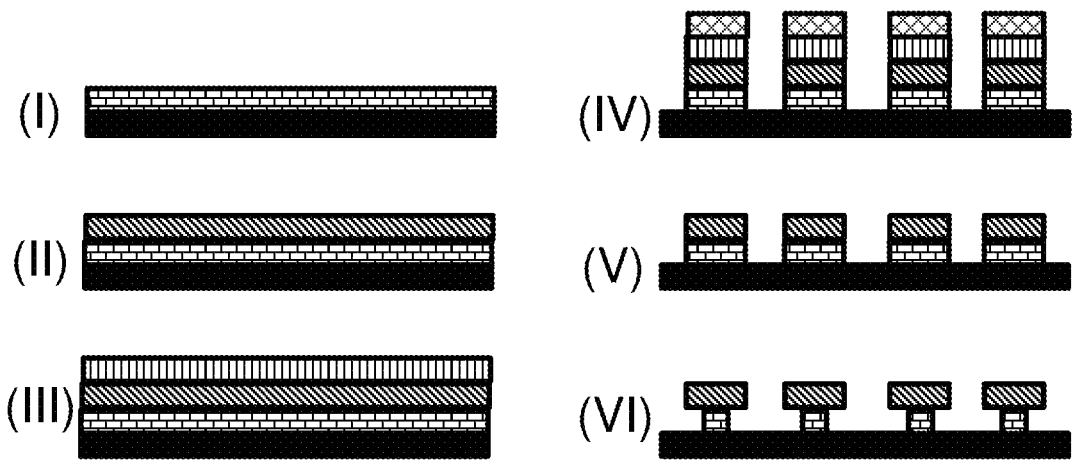
FIG. 10A is a graphic illustration of a device during phases I-VI of a pre-substrate transfer process according to various aspects of the current technology.
Figure 10B:
FIG. 10B is a graphic illustration of a device during phases I-II of a substrate transfer process according to various aspects of the current technology.
Figure 10C:
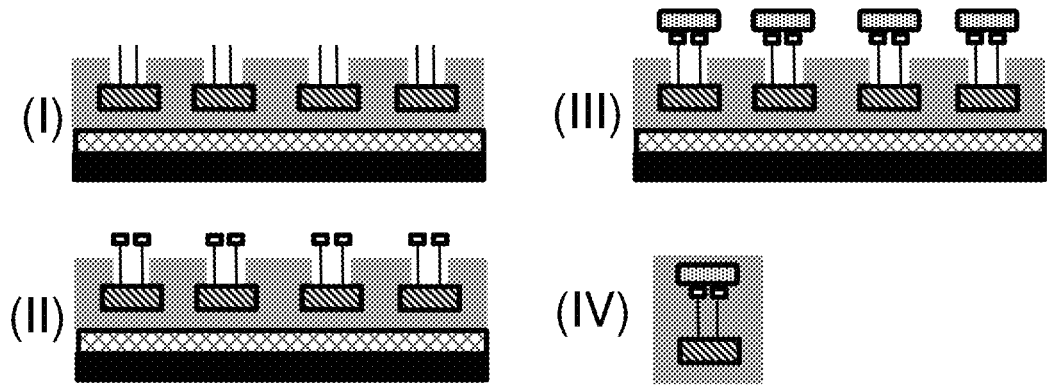
FIG. 10C is a graphic illustration of a device during phases I-IV of a post-substrate transfer process according to various aspects of the current technology.
Figure 10D:
FIG. 10D is a key that describes various components depicted in FIGS. 9A-9C.

A process flow for fabricating the devices is shown in FIGS. 10A-10D, wherein FIG. 10D provides a key that identifies the components of FIGS. 10A-10C. As shown in FIG. 10A, (I), 1 μm of $SiO_2$ was coated on a 3 inch Si wafer by plasma enhanced vapor deposition (PECVD) using a Plasmalab 80Plus® reactor from Oxford Instruments (Wiesbaden, Germany). In FIG. 10A, (II), at about 207 μm microcrystalline BDD film was grown using a custom-designed microwave plasma assisted chemical vapor deposition reactor (MWPACVD) with a gas mixture of hydrogen-diborane and methane. In FIG. 10A, (III), a 1.3 μm thick aluminum hard mask for diamond etching was deposited using a Denton Desk Top Pro Sputtering System from Denton Vacuum, Inc. (Moorestown, N.J.). In FIG. 9A, (IV), the aluminum hard mask was patterned via photolithography, with small holes on the contact pads for undercutting $SiO_2$ in FIG. 9A, (VI). In FIG. 10A, (V), BDD was plasma etched in an electron cyclotron resonance reactive ion etcher using $SF_6/Ar/O_2$ as processing gases. In FIG. 10A, (VI), SiO$_2$ was over-etched in buffered oxide etchant (BOE) to create undercuts for forming parylene anchors in FIG. 10B, (I).

In FIG. 10B, (I), the Si wafer was treated with silane A174 adhesion promoter from Sigma Aldrich (St. Louis, Mo.), followed by conformal coating of about 15 μm parylene-C (PDS 2010, Specialty Coating System, Inc.; Indianapolis, Ind.) partially wrapping around BDD structure through the SiO$_2$ undercuts. In FIG. 10B, (II), a backside of the Si wafer was etched in 35% KOH at 70° C. for about 9 hours using a custom-made etching jig, as described above with reference to FIG. 4. After the BDD structures were successfully transferred onto a parylene-C substrate, the resulting BDD/parylene-C film was attached onto a carrier wafer coated with photoresist for subsequent steps.

A BDD-based pLED probe was designed and fabricated to be used for a potential application in optogenetic neuromodulation. In this case, as shown in FIG. 10C, (I), Ti/Cu was evaporated with an Auto 306 thermal evaporator (Edward, Inc.) and patterned (ABM, Inc.) to form contact pads onto a nucleation side of the BDD film. In FIG. 10C, (II), after applying low melting point (LMP) solder (62° C., 144 ALLOY Field's Metal) onto the contact pads in an acidic solution, in FIG. 10C, (III), pLEDs (Samsung, Inc) were self-assembled on the pads. In FIG. 10C, (IV), the probe was patterned, released from the carrier wafer with acetone, and rinsed with isopropanol and deionized water. Flexible wires were soldered onto the pads using LMP. Epoxy was applied to strengthen the bonding between the wires and the pads. Then, another layer of 5 μm parylene-C was deposited to encapsulate the device.

FIGS. 11A and 11B show the custom-designed etching jig. A KOH resistant O-ring was used to achieve a good seal between the etching jig and wafer with extra force from chromium coated c-clamp compressors. FIG. 11C shows fabricated BDD structures transferred on a transparent, flexible parylene-C substrate. FIGS. 11D and 11E show a close-up view of pads after KOH etching and subsequent metal deposition and patterning. The mesh structures (area 1 in FIG. 11D) are used to form parylene-C anchors, which will help to keep BDD on parylene-C during the wafer transfer step. Compared to their adjacent areas where no mesh structures are present (area 2 in FIG. 11D), the area with mesh structures has a better adhesion to the parylene-C substrate. The reason for using metals on the contact pads for interconnects and pLED assembly is that the LMP solder does not stick to BDD well. The metal on the contact pads can be replaced with silver epoxy for prototyping, but still needs metal for pLED connection, where it is used for pLED self-assembling process. FIG. 11F shows the flexibility of BDD on parylene-C substrate, where LMP was applied at both the contact pads for wiring and for pLED. FIG. 11G shows a flexible BDD-based pLED. While parylene-C is used a primary carrier polymer, other biopolymers, such as polyimide and silk fibrous polymer, can also be used as substrate materials for carrying the transferred BDD patterns.

The current-voltage property and light intensity of the probe were characterized in FIGS. 12A and 12, using a semiconductor parameter analyzer (Hewlett Packard, Inc.), and a digital power meter (Model 815 Series, Newport, Inc.) through an RHA 2000 evaluation board (Intan Technologies, Inc.). The conductivity of the BDD was $1.69 \times 10^{-3}$ Ω·cm. The threshold of the pLED turn-on voltage is much higher and the light intensity of the pLED is much lower. Further investigation using a microscope shows the surface color of the BDD is pinkish (not shown), which is a typical color for SiO$_2$ residues. To ensure all SiO$_2$ is removed, energy dispersive X-ray spectroscopy measurements were performed, which indicates Si and O$_2$ elements on the surface of BDD, as shown in FIG. 13A. This causes high contact resistance between BDD pads and pLEDs, and leads to low light emitting efficiency. FIG. 13B shows an image taken from a backside of the BDD trace of the probe, showing the surface morphology of the polycrystalline diamond. The average surface roughness was measured with a Dektak 6M from Veeco (Plainview, N.Y.) to be about 23.66 nm. The parylene anchors coated in the undercut SiO$_2$ was also observed along the edges of the BDD patterns.

The chemical sensing capability of the flexible diamond-polymer electrode array was evaluated using cyclic voltammetry (CV). A commercially available Ag/AgCl wire with a diameter of 0.5 mm was used as a reference electrode (RE). The two electrodes of the flexible BDD-polymer probe, with the surface area of 0.04-0.07 mm$^2$, were used as the working electrode (WE) and the counter electrode (CE), respectively. These studies were focused on detection of various hexamine ruthenium chloride (Ruhex) concentrations (0.4-3 mM/L) in a 1 M/L NaCl buffer solution. Current density was recorded as a function of voltage applied to the BDD WE (from –0.8 to +0.8 V) with respect to the Ag/AgCl RE. The recorded data shown in FIGS. 14A and 14B suggests that the lowest detectable concentration of Ruhex was about 0.4 mM/L. The reduction-oxidation peak potentials were similar to those measured from a commercially available BDD electrode. These results demonstrate the use of the flexible BDD-polymer sensor to detect neurochemicals.

Example 2

A flexible, diamond-polymer chemical sensor with three microelectrodes is now provided. The diamond-polymer chemical sensor features a wide aqueous potential window and low background current from diamond and mechanical flexibility from a polymer. A wafer transfer process was used to transfer boron-doped polycrystalline diamond (BDD) onto a thin parylene-C substrate with good uniformity, strong adhesion, and high yield. The as-fabricated sensor shows a much wider potential window compared to an Au electrode, and a sensitivity of about 0.018 mA/mm$^2$ mM for Ru(NH$_3$)$_6^{2+/3+}$ and 0.0012 μA/mm$^2$ mM for dopamine.

Flexibility of a chemical sensor is highly demanded especially for in vivo neurotransmitter detection. While BDD is favored for its low background current, large aqueous potential window, chemical inertness, antifouling surface, and biocompatibility, the high Young's modulus (about 10$^{12}$ Pa) is still an obstacle for the widespread use of BDD biochemical sensors. Here, a substrate transfer process is performed by etching with deep-reactive-ion dry etching (DRIE) to achieve a high yield, better uniformity and adhesion relative to other substrate transfer processes.

A 3-electrode BDD chemical sensor was constructed to demonstrate the proposed method (FIG. 15). As illustrated in FIG. 16, the sensor was fabricated by (I) depositing 1 μm SiO$_2$ onto a 3 inch silicon wafer, followed by about 3 μm BDD synthesis using microwave plasma assisted chemical vapor deposition (CVD). (II) Aluminum was sputtered and patterned as an etching mask. (III) BDD was etched using an electron cyclotron resonance reactive ion etcher (ECR-RIE). (IV) SiO$_2$ was over etched in buffered oxide etchant (BOE) to form undercuts underneath the BDD structures. (V) The wafer was coated with 18 μm parylene-C, where parylene anchors resulted from conformal CVD deposition. (VI)

After removing parylene from the backside, (VII) the frontside of the wafer was bonded to a carrier wafer using polyphenyl ether and the silicon substrate was completely etched from the backside using DRIE. Then the parylene was released from the carrier wafer, followed by (VIII) $SiO_2$ etching in BOE solution.

FIGS. 17A and 17B show a fabricated BDD-parylene sensor and its mechanical flexibility. Mesh structures with 30 µm×50 µm holes (FIG. 18A) enable more parylene anchors over large surfaces to significantly enhance the adhesion between BDD and parylene-C. A Raman spectrum taken from the nucleation side (FIG. 18B) of BDD shows that a characteristic diamond peak (1332 $cm^{-1}$) decreases and widens, and the two new boron bands appear at about 500 $cm^{-1}$ and about 1210 $cm^{-1}$. The boron doping concentration is estimated at about $10^{20}$ $cm^{-3}$. Energy dispersive X-ray spectrometry (EDS) (FIG. 18C) confirms the complete removal of $SiO_2$, which otherwise can cause high contact resistance and desensitize sensing performance. The strong adhesion between BDD and parylene was verified by "Scotch tape" testing (FIGS. 19A and 19B) using Scotch® brand transparent adhesive tape, where no BDD delamination was observed after five peelings.

To compare the chemical sensing performance of the BDD electrodes with standard Au electrodes (CHI101, CH Instruments, Inc.), cyclic voltammetry (CV) was conducted in 1 mM KCl solution (FIG. 20A), where the BDD sensor shows lower background current and a wider potential window than the Au electrodes. The surface areas of the BDD and Au working electrodes were 0.8 $mm^2$ and 3.1 $mm^2$, respectively. The detection limit of $Ru(NH_3)_6^{2+/3+}$ was at least 0.05 mM (FIG. 20B). The cathodic peak currents versus various concentration of $Ru(NH_3)_6^{2+/3+}$ (FIG. 20C) implies a good linearity of the sensor response to $Ru(NH_3)_6^{2+/3+}$ with an $R^2$ value of 0.999. The detection of Dopamine (DA) was conducted using CV (FIG. 20D) and chronoamperometry (FIG. 20E), where a 1 µM detection limit is estimated. Background corrected currents (after subtracting current of background buffer solution) versus different concentrations of DA (FIG. 20F) show a linear response to DA with an $R^2$ value of 0.993.

Example 3

A 3-electrode BDD chemical sensor was constructed to demonstrate the fabrication method including the substrate transfer process described in FIGS. 6A-6J. As illustrated in FIG. 21, the sensor was fabricated by (I) depositing 1 µm $SiO_2$ onto a 3 inch silicon wafer, followed by about 3 µm BDD synthesis using microwave plasma assisted chemical vapor deposition (CVD). (II) Copper (Cu) was sputtered and patterned as an etching mask comprising a pattern defining three electrodes. (III) BDD was etched using an electron cyclotron resonance reactive ion etcher (ECR-RIE). (IV) SiO2 was over etched in buffered oxide etchant (BOE) to form undercuts underneath the BDD structures. (V) The wafer was coated with 18 µm parylene-C, where parylene anchors resulted from conformal CVD deposition. (VI) A portion of the parylene-C above the BDD was dry etched using oxygen ($O_2$) as a reaction gas. (VII) The sensor was inverted and placed in a jig, such that a portion of the parylene-C could be removed by oxygen plasma etching and substantially all of the silicon wafer could be removed by Wet etching in KOH (although dry etching using a mixture of $SF_6$ and $CF_4$ gases also is available for this purpose). (VIII) The sensor was removed from the jig and (IX) the $SiO_2$ was removed with BOE (although diluted HF also is available for this purpose). (X) Additional parylene-C was disposed over the BDD by chemical vapor deposition. (XI) A carrier silicon wafer was coupled to the sensor by a layer of photoresist, and (XII) the parylene-C disposed over the BDD was removed by Oxygen plasma etching. (XIII) The sensor was then completed after it was separated from the carrier silicon wafer by dissolving the photoresist in acetone. The resulting 3-electrode sensor is shown in FIG. 22A and includes, from left to right, a counter electrode, a working electrode, and a reference electrode. FIG. 22B shows a 4-electrode sensor that was made by a similar method.

The 3-electrode sensor was placed in a solution comprising 100 µM dopamine (DA) and 1 mM ascorbic acid (AA). As shown in FIG. 23A, cyclic voltammetry (CV) was performed and indicated that the DA and AA have merged oxidation peaks, i.e., were substantially indistinguishable. The 3-electrode sensor was then modified in order to facilitate a separation between DA and AA CV peaks. More particularly, the 3-electrode sensor was disposed in a 50 mM solution of KOH and an electrical potential of 2.4 V and a scan rate of 0.05 V/s was applied between the reference and working electrodes. A current between the counter and working electrodes generated an oxygen-terminated BDD surface on the working electrode to generate a treated, i.e., modified, sensor. The modified sensor was then disposed in a first solution comprising 100 µm DA and 1 mM AA, a second solution comprising 50 µm DA and 1 mM AA, and a third solution comprising 20 µM DA and 1 mM AA. CV was performed in each solution and FIG. 23B shows that the DA and AA oxidation peaks were separated in each solution. Therefore, the modified 3-electrode sensor successfully distinguished DA from AA in a solution comprising both DA and AA.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of fabricating a flexible device, the method comprising:
   generating a layer of $SiO_2$ on a surface of a substrate;
   disposing a layer of an electrically conductive material on the layer of $SiO_2$;
   removing a portion of the layer of an electrically conductive material to define a pattern in the remaining electrically conductive material, wherein the pattern includes a plurality of apertures that extend through the electrically conductive material and optionally through the layer of $SiO_2$ to the substrate;
   applying an etching compound into the apertures and etching the $SiO_2$ vertically downward to the Si substrate when the apertures do not extend through the layer of $SiO_2$ and etching a portion of the layer of $SiO_2$ horizontally beneath the electrically conductive material to form a plurality of undercuts;
   disposing a flexible polymeric material over the electrically conductive material, wherein the flexible polymeric material fills the undercuts and covers the electrically conductive material; and removing the substrate and the remainder of the $SiO_2$ by etching to generate the flexible device.

2. The method according to claim 1, wherein the substrate comprises silicon (Si), glass, or GaAs.

3. The method according to claim 1, wherein the electrically conductive material comprises boron doped polycrystalline diamond (BDD).

4. The method according to claim 1, wherein the layer of an electrically conductive material has a thickness of from about 0.25 μm to about 10 μm.

5. The method according to claim 1, wherein the flexible polymeric material is parylene-C.

6. The method according to claim 1, wherein the flexible polymeric material has a thickness of from about 1 μm to about 50 μm.

7. The method according to claim 1, wherein the removing the substrate and the remainder of the $SiO_2$ by etching comprising etching with potassium hydroxide (KOH), tetramethylammonium hydroxide (TMAH), or HF/nitric/acetic acid (HNA).

8. The method according to claim 1, further comprising at least one of chemically modifying at least a portion of the electrically conductive material, disposing a ligand to at least a portion of the electrically conductive material, or disposing a thin film over at least a portion of the electrically conductive material.

9. The method according to claim 1, further comprising attaching components to the electrically conductive material, wherein the components are selected from the group consisting of contact pads, contacts, light emitting diodes (LEDs), micro LEDs (μLEDs), wires, and combinations thereof.

10. The method according to claim 1, wherein the flexible device is a brain implant.

11. The method according to claim 1, wherein the removing a portion of the layer of an electrically conductive material is performed by photolithography.

12. The method according to claim 11, wherein the photolithography comprises:
disposing a metal layer onto the layer of an electrically conductive material, wherein the metal layer comprises aluminum (Al), copper (Cu), or gold (Au);
disposing a layer of photoresist on the metal layer;
disposing a ultraviolet light (UV)-transparent mask on the layer of photoresist, wherein the UV-transparent mask comprises a pattern that is not UV-transparent;
and exposing the UV-transparent mask to UV light.

13. The method according to claim 11, wherein the photolithography is performed by a lift-off method.

14. A method of fabricating a flexible device, the method comprising:
generating a layer of $SiO_2$ on a surface of a silicon (Si) substrate;
disposing a layer of boron doped polycrystalline diamond (BDD) on the layer of $SiO_2$;
removing a portion of the BDD to define a pattern in the remaining BDD, wherein the pattern includes a plurality of apertures that extend through the BDD and optionally through the layer of $SiO_2$ to the substrate;
applying an etching compound into the apertures and etching the $SiO_2$ vertically downward to the Si substrate when the apertures do not extend through the layer of $SiO_2$ and etching a portion of the layer of $SiO_2$ horizontally beneath the electrically conductive material to form a plurality of undercuts;
disposing parylene-C over the BDD, wherein the parylene-C fills the undercuts and covers the BDD;
removing a portion of the parylene-C located above the BDD;
inverting the device and removing a top portion of the parylene-C and substantially all of the Si substrate;
inverting the device and removing the remainder of the $SiO_2$;
disposing additional parylene-C over top and bottom surfaces of the BDD by chemical vapor deposition;
and removing the parylene-C disposed on the top surface of the BDD.

15. The method according to claim 14, wherein the flexible device is a sensor comprising a working electrode, a counter electrode, and a reference electrode.

16. The method according to claim 15, wherein the method further comprises:
at least one of chemically modifying at least the working electrode, disposing a ligand to at least the working electrode, and disposing a thin film over at least the working electrode.

17. The method according to claim 15, wherein the flexible device is configured to be implanted in neural tissue.

18. A method of fabricating a flexible device, the method comprising:
generating a layer of $SiO_2$ on a surface of a substrate;
placing a layer of an electrically conductive material comprising boron doped polycrystalline diamond on the layer of $SiO_2$;
removing a portion of the electrically conductive material to define a pattern in the remaining electrically conductive material;
etching a portion of the layer of $SiO_2$ horizontally beneath the electrically conductive material to form at least one undercut;
placing a flexible polymeric material over the electrically conductive material to fill the at least one undercut and cover the electrically conductive material; and
removing the substrate and the remainder of the $SiO_2$ by etching to create the flexible device.

19. The method according to claim 18, wherein the flexible substrate comprises silicon (Si), glass, or GaAs, and the pattern includes a plurality of apertures that extend through the electrically conductive material, and the method further comprises applying an etching compound into the apertures.

20. The method according to claim 18, wherein the removing the portion of the electrically conductive material is performed by photolithography.

21. The method according to claim 18, further comprising attaching components to the electrically conductive material, wherein the components comprise at least one of: contact pads, contacts, light emitting diodes (LEDs), micro LEDs (μLEDs), wires, or combinations thereof.

22. The method according to claim 18, wherein the flexible device is a mammalian implantable sensor or probe.

23. A flexible device comprising:
an electrically conductive material that defines a predetermined pattern, wherein the pattern includes at least one aperture that extends from a first surface of the electrically conductive material to a second opposing surface of the electrically conductive material; and
a flexible polymeric substrate,
wherein the second surface of the electrically conductive material is disposed on the flexible polymer substrate and the flexible polymeric substrate extends through the at least one aperture from the second surface to the first surface and extends radially on the first surface about the at least one aperture to form an anchor that partially covers the electrically conductive material, and wherein the flexible device is an implantable probe or sensor having a Young's modulus that is closer to the Young's modulus of a human brain relative to the Young's modulus of boron doped polycrystalline diamond (BDD).

24. The flexible device according to claim 23, wherein the electrically conductive material is boron doped polycrystalline diamond (BDD), and the flexible polymeric substrate is parylene-C.

* * * * *